(12) United States Patent
Dempsey et al.

(10) Patent No.: US 12,000,914 B2
(45) Date of Patent: Jun. 4, 2024

(54) RESISTIVE ELECTROMAGNET SYSTEMS AND METHODS

(71) Applicant: ViewRay Technologies, Inc., Oakwood Village, OH (US)

(72) Inventors: James F. Dempsey, Atherton, CA (US); Massimo Dal Forno, San Carlos, CA (US); Shmaryu M. Shvartsman, Highland Heights, OH (US); David L. Rayner, Reading (GB)

(73) Assignee: ViewRay Systems, Inc., Denver, CO (US)

( * ) Notice: Subject to any disclaimer, the term of this patent is extended or adjusted under 35 U.S.C. 154(b) by 59 days.

(21) Appl. No.: 17/559,957

(22) Filed: Dec. 22, 2021

(65) Prior Publication Data

US 2022/0113360 A1 Apr. 14, 2022

Related U.S. Application Data

(63) Continuation of application No. 16/179,764, filed on Nov. 2, 2018, now Pat. No. 11,209,509.

(Continued)

(51) Int. Cl.
*G01R 33/381* (2006.01)
*A61B 5/055* (2006.01)
(Continued)

(52) U.S. Cl.
CPC ............ *G01R 33/381* (2013.01); *A61B 5/055* (2013.01); *G01R 33/34053* (2013.01);
(Continued)

(58) Field of Classification Search
None
See application file for complete search history.

(56) References Cited

U.S. PATENT DOCUMENTS

| 3,428,307 A | 2/1969 | Hunter |
| 4,019,059 A | 4/1977 | Brundin |

(Continued)

FOREIGN PATENT DOCUMENTS

| CN | 1612713 A | 5/2005 |
| CN | 1669599 A | 9/2005 |

(Continued)

OTHER PUBLICATIONS

Anixter Inc. World Headquarters; "Wire Wisdom"; 2014 NEC 310.106 (B); 1 Page; 2016.

(Continued)

*Primary Examiner* — Jermele M Hollington
(74) *Attorney, Agent, or Firm* — Davis Graham & Stubbs LLP

(57) ABSTRACT

A magnetic resonance imaging (MRI) system having a resistive, solenoidal electromagnet for whole-body MRI may include ferromagnetic material within an envelope of the electromagnet. The system can be configured to have a field strength of at least 0.05 Tesla and its main electromagnetic field can be generated by layers of conductors instead of bundles. Certain electromagnet designs may be fabricated using non-metallic formers, such as fiberglass, and can be constructed to form a rigid object with the layers of conductors by fixing all together with an epoxy. The electromagnet may be configured to have two separated halves, which may be held apart by a fixation structure such as carbon fiber. The power supply for certain electromagnets herein may have current fluctuations, at frequencies of 180 Hz or above, of at least one part per ten thousand without requiring an additional current filter.

25 Claims, 16 Drawing Sheets

Related U.S. Application Data

(60) Provisional application No. 62/677,546, filed on May 29, 2018, provisional application No. 62/672,525, filed on May 16, 2018.

(51) Int. Cl.
*G01R 33/34* (2006.01)
*G01R 33/38* (2006.01)

(52) U.S. Cl.
CPC ..... *G01R 33/3802* (2013.01); *G01R 33/3804* (2013.01); *G01R 33/3806* (2013.01)

(56) References Cited

U.S. PATENT DOCUMENTS

| | | |
|---|---|---|
| 4,233,662 A | 11/1980 | Lemay |
| 4,481,657 A | 11/1984 | Larsson |
| 4,589,126 A | 5/1986 | Augustsson |
| 4,612,596 A | 9/1986 | Fox |
| 4,694,837 A | 9/1987 | Blakeley |
| 4,766,378 A | 8/1988 | Danby |
| 4,771,785 A | 9/1988 | Duer |
| 4,851,778 A | 7/1989 | Kaufman |
| 4,987,309 A | 1/1991 | Klasen |
| 5,023,554 A * | 6/1991 | Cho ............. G01R 33/3806 324/309 |
| 5,027,818 A | 7/1991 | Bova |
| 5,039,867 A | 8/1991 | Nishihara |
| 5,094,837 A | 3/1992 | Bis |
| 5,117,829 A | 6/1992 | Miller |
| 5,216,255 A | 6/1993 | Weidlich |
| 5,291,169 A | 3/1994 | Ige |
| 5,317,616 A | 5/1994 | Swerdloff |
| 5,327,884 A | 7/1994 | Hardy |
| 5,328,681 A | 7/1994 | Kito |
| 5,332,908 A | 7/1994 | Weidlich |
| 5,351,280 A | 9/1994 | Swerdloff |
| 5,363,077 A | 11/1994 | Herd |
| 5,365,927 A | 11/1994 | Roemer |
| 5,373,844 A | 12/1994 | Smith |
| 5,377,678 A | 1/1995 | Dumoulin |
| 5,378,989 A | 1/1995 | Barber |
| 5,391,139 A | 2/1995 | Edmundson |
| 5,402,094 A * | 3/1995 | Enge ............. H01F 7/202 324/319 |
| 5,412,363 A | 5/1995 | Breneman |
| 5,412,823 A | 5/1995 | Sitta |
| 5,442,675 A | 8/1995 | Swerdloff |
| 5,443,068 A | 8/1995 | Cline |
| 5,458,125 A | 10/1995 | Schweikard |
| 5,511,549 A | 4/1996 | Legg |
| 5,513,238 A | 4/1996 | Leber |
| 5,537,452 A | 7/1996 | Shepherd |
| 5,538,494 A | 7/1996 | Matsuda |
| 5,547,454 A | 8/1996 | Horn |
| 5,555,283 A | 9/1996 | Shiu |
| 5,570,022 A | 10/1996 | Ehnholm |
| 5,585,724 A | 12/1996 | Morich |
| 5,596,619 A | 1/1997 | Carol |
| 5,602,892 A | 2/1997 | Llacer |
| 5,602,982 A | 2/1997 | Llacer |
| 5,647,361 A | 7/1997 | Damadian |
| 5,659,281 A | 8/1997 | Pissanetzky |
| 5,708,362 A | 1/1998 | Frese |
| 5,722,411 A | 3/1998 | Suzuki |
| 5,724,400 A | 3/1998 | Swerdloff |
| 5,734,384 A | 3/1998 | Yanof |
| 5,740,225 A | 4/1998 | Nabatame |
| 5,748,700 A | 5/1998 | Shepherd |
| 5,751,781 A | 5/1998 | Brown |
| 5,757,881 A | 5/1998 | Hughes |
| 5,790,996 A | 8/1998 | Narfstrom |
| 5,802,136 A | 9/1998 | Carol |
| 5,815,547 A | 9/1998 | Shepherd |
| 5,851,182 A | 12/1998 | Sahadevan |
| 5,894,503 A | 4/1999 | Shepherd |
| 5,936,502 A | 8/1999 | Englund |
| 5,952,830 A | 9/1999 | Petropoulos |
| 5,993,373 A | 11/1999 | Nonaka |
| 6,005,916 A | 12/1999 | Johnson |
| 6,011,393 A | 1/2000 | Kaufman |
| 6,038,283 A | 3/2000 | Carol |
| 6,052,430 A | 4/2000 | Siochi |
| 6,094,760 A | 8/2000 | Nonaka |
| 6,104,779 A | 8/2000 | Shepherd |
| 6,112,112 A | 8/2000 | Gilhuijs |
| 6,125,335 A | 9/2000 | Simon |
| 6,144,875 A | 11/2000 | Schweikard |
| 6,175,761 B1 | 1/2001 | Frandsen |
| 6,198,957 B1 | 3/2001 | Green |
| 6,207,952 B1 | 3/2001 | Kan |
| 6,223,067 B1 | 4/2001 | Vilsmeier |
| 6,240,162 B1 | 5/2001 | Hernandez-Guerra |
| 6,260,005 B1 | 7/2001 | Yang |
| 6,273,858 B1 | 8/2001 | Fox |
| 6,278,891 B1 | 8/2001 | Reiderman |
| 6,311,389 B1 | 11/2001 | Uosaki |
| 6,314,159 B1 | 11/2001 | Siochi |
| 6,320,377 B1 | 11/2001 | Miyazaki |
| 6,330,300 B1 | 12/2001 | Siochi |
| 6,349,129 B1 | 2/2002 | Siochi |
| 6,366,798 B2 | 4/2002 | Green |
| 6,373,250 B1 | 4/2002 | Tsoref |
| 6,381,486 B1 | 4/2002 | Mistretta |
| 6,385,286 B1 | 5/2002 | Fitchard |
| 6,385,477 B1 | 5/2002 | Werner |
| 6,393,096 B1 | 5/2002 | Carol |
| 6,405,072 B1 | 6/2002 | Cosman |
| 6,411,675 B1 | 6/2002 | Llacer |
| 6,414,487 B1 | 7/2002 | Anand |
| 6,414,490 B1 | 7/2002 | Damadian |
| 6,422,748 B1 | 7/2002 | Shepherd |
| 6,424,856 B1 | 7/2002 | Vilsmeier |
| 6,456,076 B1 | 9/2002 | Joseph |
| 6,459,769 B1 | 10/2002 | Cosman |
| 6,466,813 B1 | 10/2002 | Shukla |
| 6,487,435 B2 | 11/2002 | Mistretta |
| 6,504,899 B2 | 1/2003 | Pugachev |
| 6,512,813 B1 | 1/2003 | Krispel |
| 6,512,942 B1 | 1/2003 | Burdette |
| 6,516,046 B1 | 2/2003 | Frohlich |
| 6,526,123 B2 | 2/2003 | Ein-Gal |
| 6,527,443 B1 | 3/2003 | Vilsmeier |
| 6,542,767 B1 | 4/2003 | McNichols |
| 6,546,073 B1 | 4/2003 | Lee |
| 6,560,311 B1 | 5/2003 | Shepard |
| 6,564,084 B2 | 5/2003 | Allred |
| 6,570,475 B1 | 5/2003 | Lvovsky |
| 6,584,174 B2 | 6/2003 | Schubert |
| 6,591,127 B1 | 7/2003 | McKinnon |
| 6,594,516 B1 | 7/2003 | Steckner |
| 6,600,810 B1 | 7/2003 | Hughes |
| 6,609,022 B2 | 8/2003 | Vilsmeier |
| 6,611,700 B1 | 8/2003 | Vilsmeier |
| 6,618,467 B1 | 9/2003 | Ruchala |
| 6,636,645 B1 | 10/2003 | Yu |
| 6,657,391 B2 | 12/2003 | Ding |
| 6,661,870 B2 | 12/2003 | Kapatoes |
| 6,708,054 B2 | 3/2004 | Shukla |
| 6,719,683 B2 | 4/2004 | Frohlich |
| 6,724,922 B1 | 4/2004 | Vilsmeier |
| 6,728,336 B2 | 4/2004 | Bortfeld |
| 6,731,970 B2 | 5/2004 | Schlossbauer |
| 6,735,277 B2 | 5/2004 | McNutt |
| 6,757,355 B1 | 6/2004 | Siochi |
| 6,772,002 B2 | 8/2004 | Schmidt |
| 6,778,850 B1 | 8/2004 | Adler |
| 6,792,074 B2 | 9/2004 | Erbel |
| 6,849,129 B2 | 2/2005 | Bilz |
| 6,853,704 B2 | 2/2005 | Collins |
| 6,859,660 B2 | 2/2005 | Vilsmeier |
| 6,862,469 B2 | 3/2005 | Bucholz |
| 6,865,253 B2 | 3/2005 | Blumhofer |
| 6,865,411 B2 | 3/2005 | Erbel |

(56) References Cited

U.S. PATENT DOCUMENTS

| | | |
|---|---|---|
| 6,879,714 B2 | 4/2005 | Hutter |
| 6,885,886 B2 | 4/2005 | Bauch |
| 6,891,375 B2 | 5/2005 | Goto |
| 6,891,924 B1 | 5/2005 | Yoda |
| 6,898,456 B2 | 5/2005 | Erbel |
| 6,915,005 B1 | 7/2005 | Ruchala |
| 6,937,696 B1 | 8/2005 | Mostafavi |
| 6,940,281 B2 | 9/2005 | Feenan |
| 6,947,582 B1 | 9/2005 | Vilsmeier |
| 6,965,847 B2 | 11/2005 | Wessol |
| 6,980,679 B2 | 12/2005 | Jeung |
| 6,999,555 B2 | 2/2006 | Morf |
| 7,012,385 B1 | 3/2006 | Kulish |
| 7,046,762 B2 | 5/2006 | Lee |
| 7,046,765 B2 | 5/2006 | Wong |
| 7,046,831 B2 | 5/2006 | Ruchala |
| 7,050,845 B2 | 5/2006 | Vilsmeier |
| 7,092,573 B2 | 8/2006 | Luo |
| 7,095,823 B2 | 8/2006 | Topolnjak |
| 7,096,055 B1 | 8/2006 | Schweikard |
| 7,123,758 B2 | 10/2006 | Jeung |
| 7,130,372 B2 | 10/2006 | Kusch |
| 7,154,991 B2 | 12/2006 | Earnst |
| 7,162,005 B2 | 1/2007 | Bjorkholm |
| 7,166,852 B2 | 1/2007 | Saracen |
| 7,171,257 B2 | 1/2007 | Thomson |
| 7,180,366 B2 | 2/2007 | Roos |
| 7,191,100 B2 | 3/2007 | Mostafavi |
| 7,202,663 B2 | 4/2007 | Huang |
| 7,204,640 B2 | 4/2007 | Fu |
| 7,221,733 B1 | 5/2007 | Takai |
| 7,227,925 B1 | 6/2007 | Mansfield |
| 7,230,429 B1 | 6/2007 | Huang |
| 7,231,075 B2 | 6/2007 | Raghavan |
| 7,231,076 B2 | 6/2007 | Fu |
| 7,260,426 B2 | 8/2007 | Schweikard |
| 7,265,545 B2 | 9/2007 | Krueger |
| 7,266,175 B1 | 9/2007 | Romesberg |
| 7,266,176 B2 | 9/2007 | Allison |
| 7,289,599 B2 | 10/2007 | Seppi |
| 7,298,819 B2 | 11/2007 | Dooley |
| 7,302,038 B2 | 11/2007 | Mackie |
| 7,308,298 B2 | 12/2007 | Miyazaki |
| 7,315,636 B2 | 1/2008 | Kuduvalli |
| 7,317,782 B2 | 1/2008 | Bjorkholm |
| 7,318,805 B2 | 1/2008 | Schweikard |
| 7,324,626 B2 | 1/2008 | Vilsmeier |
| 7,327,865 B2 | 2/2008 | Fu |
| 7,366,278 B2 | 4/2008 | Fu |
| 7,394,081 B2 | 7/2008 | Okazaki |
| 7,403,638 B2 | 7/2008 | Jeung |
| 7,412,029 B2 | 8/2008 | Myles |
| 7,415,095 B2 | 8/2008 | Wofford |
| 7,417,434 B2 | 8/2008 | Overweg |
| 7,423,273 B2 | 9/2008 | Clayton |
| 7,426,318 B2 | 9/2008 | Fu |
| 7,444,178 B2 | 10/2008 | Goldbach |
| 7,463,823 B2 | 12/2008 | Birkenbach |
| 7,471,813 B2 | 12/2008 | Ulmer |
| 7,477,776 B2 | 1/2009 | Lachner |
| 7,480,399 B2 | 1/2009 | Fu |
| 7,489,131 B2 | 2/2009 | Lvovsky |
| 7,505,037 B2 | 3/2009 | Wang |
| 7,505,617 B2 | 3/2009 | Fu |
| 7,522,779 B2 | 4/2009 | Fu |
| 7,532,705 B2 | 5/2009 | Yin |
| 7,542,622 B1 | 6/2009 | Angelini |
| 7,558,617 B2 | 7/2009 | Vilsmeier |
| 7,570,987 B2 | 8/2009 | Raabe |
| 7,577,474 B2 | 8/2009 | Vilsmeier |
| 7,589,326 B2 | 9/2009 | Mollov |
| 7,602,190 B2 * | 10/2009 | Piferi ..................... A61B 90/11 |
| | | 324/318 |
| 7,634,122 B2 | 12/2009 | Bertram |
| 7,636,417 B2 | 12/2009 | Bjorkholm |
| 7,638,752 B2 | 12/2009 | Partain |
| 7,657,304 B2 | 2/2010 | Mansfield |
| 7,659,718 B1 | 2/2010 | Lustig |
| 7,688,998 B2 | 3/2010 | Tuma |
| 7,728,311 B2 | 6/2010 | Gall |
| 7,741,624 B1 | 6/2010 | Sahadevan |
| 7,785,358 B2 | 8/2010 | Lach |
| 7,791,338 B2 | 9/2010 | Kim |
| 7,840,045 B2 | 11/2010 | Guo |
| 7,901,357 B2 | 3/2011 | Boctor |
| 7,902,530 B1 | 3/2011 | Sahadevan |
| 7,907,987 B2 | 3/2011 | Dempsey |
| 7,957,507 B2 | 6/2011 | Cadman |
| 8,013,697 B2 * | 9/2011 | Calvert ............. G01R 33/3802 |
| | | 335/282 |
| 8,139,714 B1 | 3/2012 | Sahadevan |
| 8,155,417 B2 | 4/2012 | Piron |
| 8,173,983 B1 | 5/2012 | Sahadevan |
| 8,190,233 B2 | 5/2012 | Dempsey |
| 8,214,010 B2 | 7/2012 | Courtney |
| 8,310,233 B2 | 11/2012 | Trzasko |
| 8,331,531 B2 | 12/2012 | Fahrig |
| 8,334,697 B2 | 12/2012 | Overweg |
| 8,378,677 B2 | 2/2013 | Morich |
| 8,405,395 B2 | 3/2013 | Setsompop |
| 8,460,195 B2 | 6/2013 | Courtney |
| 8,604,795 B2 | 12/2013 | Overweg |
| 8,637,841 B2 | 1/2014 | Prince |
| 8,723,521 B2 | 5/2014 | Schulz |
| 8,803,524 B2 | 8/2014 | Dempsey |
| 8,812,077 B2 | 8/2014 | Dempsey |
| 8,836,332 B2 | 9/2014 | Shvartsman |
| 8,896,308 B2 | 11/2014 | Shvartsman |
| 8,983,573 B2 | 3/2015 | Carlone |
| 9,082,520 B2 | 7/2015 | Prince |
| 9,114,253 B2 | 8/2015 | Dempsey |
| 9,289,626 B2 | 3/2016 | Kawrakow |
| 9,421,398 B2 | 8/2016 | Shvartsman |
| 9,423,477 B2 | 8/2016 | Dempsey |
| 9,446,263 B2 | 9/2016 | Dempsey |
| 9,472,000 B2 | 10/2016 | Dempsey |
| 9,526,918 B2 | 12/2016 | Kruip |
| 9,638,773 B2 | 5/2017 | Poole |
| 10,132,888 B2 | 11/2018 | Shvartsman |
| 10,613,171 B2 | 4/2020 | Li |
| 11,209,509 B2 * | 12/2021 | Dempsey ........... G01R 33/3806 |
| 11,378,629 B2 | 7/2022 | Dempsey |
| 11,675,036 B2 * | 6/2023 | Liu ..................... G01R 33/3875 |
| | | 324/318 |
| 2001/0001807 A1 | 5/2001 | Green |
| 2001/0049475 A1 | 12/2001 | Bucholz |
| 2002/0046010 A1 | 4/2002 | Wessol |
| 2002/0091315 A1 | 7/2002 | Spetz |
| 2002/0131556 A1 | 9/2002 | Steinberg |
| 2002/0150207 A1 | 10/2002 | Kapatoes |
| 2002/0151786 A1 | 10/2002 | Shukla |
| 2002/0193685 A1 | 12/2002 | Mate |
| 2003/0011451 A1 | 1/2003 | Katznelson |
| 2003/0057947 A1 | 3/2003 | Ni |
| 2003/0068097 A1 | 4/2003 | Wilson |
| 2003/0083901 A1 | 5/2003 | Bosch |
| 2003/0086526 A1 | 5/2003 | Clark |
| 2003/0112922 A1 | 6/2003 | Burdette |
| 2003/0155530 A1 | 8/2003 | Adnani |
| 2003/0181804 A1 | 9/2003 | Gagnon |
| 2003/0197507 A1 | 10/2003 | Liu |
| 2003/0219098 A1 | 11/2003 | McNutt |
| 2004/0030240 A1 | 2/2004 | Kimura |
| 2004/0054248 A1 | 3/2004 | Kimchy |
| 2004/0106869 A1 | 6/2004 | Tepper |
| 2004/0222795 A1 | 11/2004 | Dietz |
| 2004/0239327 A1 | 12/2004 | Heid |
| 2004/0254448 A1 | 12/2004 | Amies |
| 2004/0254773 A1 | 12/2004 | Zhang |
| 2005/0020917 A1 | 1/2005 | Scherch |
| 2005/0030028 A1 | 2/2005 | Clarke |
| 2005/0053267 A1 | 3/2005 | Mostafavi |
| 2005/0054916 A1 | 3/2005 | Mostafavi |
| 2005/0065431 A1 | 3/2005 | Reiderman |

(56) References Cited

U.S. PATENT DOCUMENTS

| | | |
|---|---|---|
| 2005/0143965 A1 | 6/2005 | Failla |
| 2005/0197564 A1 | 9/2005 | Dempsey |
| 2005/0201516 A1 | 9/2005 | Ruchala |
| 2005/0207531 A1 | 9/2005 | Dempsey |
| 2005/0254623 A1 | 11/2005 | Kamath |
| 2006/0033496 A1 | 2/2006 | Shvartsman |
| 2006/0058636 A1 | 3/2006 | Wemple |
| 2006/0074292 A1 | 4/2006 | Thomson |
| 2006/0120583 A1 | 6/2006 | Dewaele |
| 2006/0170679 A1 | 8/2006 | Wang |
| 2006/0193441 A1 | 8/2006 | Cadman |
| 2006/0280287 A1 | 12/2006 | Esham |
| 2006/0291621 A1 | 12/2006 | Yan |
| 2007/0003021 A1 | 1/2007 | Guertin |
| 2007/0016014 A1 | 1/2007 | Hara |
| 2007/0038058 A1 | 2/2007 | West |
| 2007/0043286 A1 | 2/2007 | Lu |
| 2007/0083114 A1 | 4/2007 | Yang |
| 2007/0086569 A1 | 4/2007 | Johnsen |
| 2007/0197908 A1 | 8/2007 | Ruchala |
| 2007/0216409 A1 | 9/2007 | Overweg |
| 2007/0230770 A1 | 10/2007 | Kulkarni |
| 2007/0244386 A1 | 10/2007 | Steckner |
| 2008/0033287 A1 | 2/2008 | Schwarze |
| 2008/0049896 A1 | 2/2008 | Kuduvalli |
| 2008/0049897 A1 | 2/2008 | Molloy |
| 2008/0093567 A1 | 4/2008 | Gall |
| 2008/0108894 A1 | 5/2008 | Elgavish |
| 2008/0123927 A1 | 5/2008 | Miga |
| 2008/0177138 A1 | 7/2008 | Courtney |
| 2008/0197842 A1 | 8/2008 | Lustig |
| 2008/0208036 A1 | 8/2008 | Amies |
| 2008/0235052 A1 | 9/2008 | Node-Langlois |
| 2008/0259560 A1 | 10/2008 | Lvovsky |
| 2008/0303457 A1 | 12/2008 | Maltz |
| 2009/0039886 A1 | 2/2009 | White |
| 2009/0060130 A1 | 3/2009 | Wilkens |
| 2009/0129545 A1 | 5/2009 | Adler |
| 2009/0129659 A1 | 5/2009 | Deutschmann |
| 2009/0149735 A1 | 6/2009 | Fallone |
| 2009/0161826 A1 | 6/2009 | Gertner |
| 2009/0171184 A1 | 7/2009 | Jenkins |
| 2009/0175418 A1 | 7/2009 | Sakurai |
| 2009/0264768 A1 | 10/2009 | Courtney |
| 2009/0299170 A1 | 12/2009 | Gebhardt |
| 2010/0033186 A1 | 2/2010 | Overweg |
| 2010/0056900 A1 | 3/2010 | Whitcomb |
| 2010/0113911 A1 | 5/2010 | Dempsey |
| 2010/0119032 A1 | 5/2010 | Yan |
| 2010/0174172 A1 | 7/2010 | Ein-Gal |
| 2010/0188082 A1 | 7/2010 | Morich |
| 2010/0239066 A1 | 9/2010 | Fahrig |
| 2010/0304976 A1 | 12/2010 | Overweg |
| 2010/0312095 A1 | 12/2010 | Jenkins |
| 2010/0312100 A1 | 12/2010 | Zarkh |
| 2010/0321019 A1 | 12/2010 | Imamura |
| 2010/0322497 A1 | 12/2010 | Dempsey |
| 2011/0012593 A1 | 1/2011 | Shvartsman |
| 2011/0018541 A1 | 1/2011 | Solf |
| 2011/0051893 A1 | 3/2011 | McNutt |
| 2011/0087090 A1 | 4/2011 | Boernert |
| 2011/0118588 A1 | 5/2011 | Komblau |
| 2011/0121832 A1 | 5/2011 | Shvartsman |
| 2011/0142887 A1 | 6/2011 | Har-Noy |
| 2011/0150180 A1 | 6/2011 | Balakin |
| 2011/0156703 A1 | 6/2011 | O'Connor |
| 2011/0218420 A1 | 9/2011 | Carlone |
| 2011/0237859 A1 | 9/2011 | Kuhn |
| 2011/0241684 A1 | 10/2011 | Dempsey |
| 2011/0284757 A1 | 11/2011 | Butuceanu |
| 2012/0022363 A1 | 1/2012 | Dempsey |
| 2012/0043482 A1 | 2/2012 | Prince |
| 2012/0070056 A1 | 3/2012 | Krueger |
| 2012/0150017 A1 | 6/2012 | Yamaya |
| 2012/0157402 A1 | 6/2012 | Cao |
| 2012/0165652 A1 | 6/2012 | Dempsey |
| 2012/0245453 A1 | 9/2012 | Tryggestad |
| 2012/0253172 A1 | 10/2012 | Loeffler |
| 2013/0066135 A1 | 3/2013 | Rosa |
| 2013/0086163 A1 | 4/2013 | Neff |
| 2013/0090549 A1 | 4/2013 | Meltsner |
| 2013/0141094 A1 | 6/2013 | Miyazaki |
| 2013/0147476 A1 | 6/2013 | Shvartsman |
| 2013/0245425 A1 | 9/2013 | Dempsey |
| 2013/0261429 A1 | 10/2013 | Lee |
| 2013/0261430 A1 | 10/2013 | Uhlemann |
| 2013/0296687 A1 | 11/2013 | Dempsey |
| 2013/0345545 A1 | 12/2013 | Gross |
| 2013/0345556 A1 | 12/2013 | Courtney |
| 2014/0003023 A1 | 1/2014 | Weibler |
| 2014/0084926 A1 | 3/2014 | Amthor |
| 2014/0112453 A1 | 4/2014 | Prince |
| 2014/0121495 A1 | 5/2014 | Dempsey |
| 2014/0128719 A1 | 5/2014 | Longfield |
| 2014/0135615 A1 | 5/2014 | Krulp |
| 2014/0263990 A1 | 9/2014 | Kawrykow |
| 2014/0266206 A1 | 9/2014 | Dempsey |
| 2014/0266208 A1 | 9/2014 | Dempsey |
| 2014/0275963 A1 | 9/2014 | Shvartsman |
| 2014/0330108 A1 | 11/2014 | Dempsey |
| 2014/0336442 A1 | 11/2014 | Keppel |
| 2014/0347053 A1 | 11/2014 | Dempsey |
| 2015/0065860 A1 | 3/2015 | Shvartsman |
| 2015/0077118 A1 | 3/2015 | Shvartsman |
| 2015/0095044 A1 | 4/2015 | Hartman |
| 2015/0126850 A1 | 5/2015 | Cetingul |
| 2015/0154756 A1 | 6/2015 | Gerganov |
| 2015/0165233 A1 | 6/2015 | Dempsey |
| 2015/0185300 A1 | 7/2015 | Shvartsman |
| 2015/0273239 A1 | 10/2015 | Hsu |
| 2015/0346304 A1 | 12/2015 | Hu |
| 2016/0146911 A1 | 5/2016 | Chmielewski |
| 2016/0184609 A1 | 6/2016 | Dempsey |
| 2016/0232690 A1 | 8/2016 | Ahmad |
| 2016/0252596 A1 | 9/2016 | Nielsen |
| 2016/0256712 A1 | 9/2016 | Vahala |
| 2016/0334479 A1 | 11/2016 | Poole |
| 2016/0356869 A1 | 12/2016 | Dempsey |
| 2017/0001039 A1 | 1/2017 | Dempsey |
| 2017/0014644 A1 | 1/2017 | Shvartsman |
| 2017/0021198 A1 | 1/2017 | Kawrykow |
| 2017/0148536 A1 | 5/2017 | Kawrykow |
| 2017/0203126 A1 | 7/2017 | Dempsey |
| 2017/0231583 A1 | 8/2017 | Goteti Venkata |
| 2017/0252577 A1 | 9/2017 | Dempsey |
| 2017/0371001 A1 | 12/2017 | Dempsey |
| 2018/0021595 A1 | 1/2018 | Kesti-Helia |
| 2018/0078785 A1 | 3/2018 | Ollila |
| 2018/0078792 A1 | 3/2018 | Ollila |
| 2018/0133511 A1 | 5/2018 | Dempsey |
| 2018/0143274 A1 | 5/2018 | Poole |
| 2018/0185669 A1 | 7/2018 | Kuusela |
| 2018/0243584 A1 | 8/2018 | Nord |
| 2019/0083814 A1 | 3/2019 | Tallinen |
| 2019/0168028 A1 | 6/2019 | Dempsey |
| 2019/0217126 A1 | 7/2019 | Shvartsman |
| 2019/0353724 A1 | 11/2019 | Snelten |
| 2019/0353725 A1 | 11/2019 | Dempsey |
| 2020/0086143 A1 | 3/2020 | Maltz |
| 2020/0147412 A1 | 5/2020 | Ni |
| 2020/0246637 A1 | 8/2020 | Wang |

FOREIGN PATENT DOCUMENTS

| | | |
|---|---|---|
| CN | 1946339 A | 4/2007 |
| CN | 101000689 A | 7/2007 |
| CN | 101267858 A | 9/2008 |
| CN | 101268474 A | 9/2008 |
| CN | 101278361 A | 10/2008 |
| CN | 101443819 A | 5/2009 |
| CN | 102369529 A | 3/2012 |
| CN | 102472830 A | 5/2012 |
| CN | 102641561 A | 8/2012 |
| DE | 3828639 A1 | 3/1989 |

(56) References Cited

FOREIGN PATENT DOCUMENTS

| | | |
|---|---|---|
| EP | 1761794 | 3/2007 |
| EP | 2359905 A1 | 8/2011 |
| EP | 2424430 B1 | 1/2013 |
| FR | 2839894 A1 | 11/2003 |
| GB | 2219406 | 12/1989 |
| GB | 2219406 A | 12/1989 |
| GB | 2393373 A | 3/2004 |
| JP | 62281934 | 12/1988 |
| JP | 63294839 | 12/1988 |
| JP | 06054916 | 1/1994 |
| JP | H07213507 A | 8/1995 |
| JP | 2001517132 A | 10/2001 |
| JP | 2002102198 A | 4/2002 |
| JP | 2002186676 A | 7/2002 |
| JP | 2002522129 A | 7/2002 |
| JP | 2005103295 A | 4/2005 |
| JP | 2006149560 A | 6/2006 |
| JP | 2007526036 A | 9/2007 |
| JP | 2008130947 | 6/2008 |
| JP | 2009501043 A | 1/2009 |
| JP | 2009511222 A | 3/2009 |
| JP | 2009112870 A | 5/2009 |
| JP | 2009160309 A | 7/2009 |
| JP | 2009538195 A | 11/2009 |
| JP | 2010269067 A | 12/2010 |
| JP | 2014502541 | 2/2014 |
| JP | 2014519382 | 8/2014 |
| JP | 2015520631 | 7/2015 |
| JP | 2016513560 | 5/2016 |
| WO | 1999032189 | 7/1999 |
| WO | 2000025864 | 5/2000 |
| WO | 2002072190 A2 | 9/2002 |
| WO | 20030008986 | 1/2003 |
| WO | 2004024235 A1 | 3/2004 |
| WO | 2005081842 A2 | 9/2005 |
| WO | 2006007277 A2 | 1/2006 |
| WO | 2006097274 A1 | 9/2006 |
| WO | 2007007276 A2 | 1/2007 |
| WO | 2007014105 A2 | 2/2007 |
| WO | 2007045076 A1 | 4/2007 |
| WO | 2007126842 A2 | 11/2007 |
| WO | 2008013598 A2 | 1/2008 |
| WO | 2008122899 A1 | 10/2008 |
| WO | 2009004521 A2 | 1/2009 |
| WO | 2009099001 | 8/2009 |
| WO | 2009107005 A2 | 9/2009 |
| WO | 2009155700 A1 | 12/2009 |
| WO | 2009156896 | 12/2009 |
| WO | 2010103644 A1 | 9/2010 |
| WO | 2010113050 A2 | 10/2010 |
| WO | 2011008969 A1 | 1/2011 |
| WO | 2012045153 | 4/2012 |
| WO | 2012164527 A1 | 12/2012 |
| WO | 2015138945 | 9/2015 |
| WO | 2015138945 A1 | 9/2015 |
| WO | 20150138945 | 9/2015 |

OTHER PUBLICATIONS

AU Search Report dated Dec. 11, 2017.
Aytekin Oto, Md, et al., Multidetector Row CT of the Liver; (2005) 43 ERDCNA 5 827-848.
B W Raaymakers et al.; "Integrating a 1.5 T MRI Scanner with a 6 MV Accelerator: Proof of Concepts," Physics in Medicine and Biology. vol. 54, No. 12, May 19, 2009, pp. N229-N237, XP055395399, Bristol GB ISSN: 0031-9155. 9 pages.
Balter, James M., et al. 'Accuracy of a Wireless Localization System for Radiotherapy' Int. J. Radiation Oncology Biol. Phys., vol. 61, No. 3. pp. 933-937, Nov. 1, 2004, Elsevier Inc., USA.
Baro, J et al. 'Penelope: An algorithm for Monte Carlo simulation of the penetration and energy loss of electrons and positrons in matter' Nuclear Instruments and Methods in Physics Research B 100 (1995) 31-46, received Sep. 30, 1994, Elsevier Science B.V.
Barth, et al. "Simultaneous Multislice (SMS) Imaging Techniques." Magnetic Resonance in Medicine; vol. 75; pp. 63-81; 2016.
Bernier, Jacques et al. 'Radiation oncology: a century of achievements' Nature Reviews—Cancer, vol. 4, Sep. 2004. pp. 737-747.
Bilgin, A. et al. 'Randomly Perturbed Radial Trajectories for Compressed Sensing MRI.' Proceedings of International Society for Magnetic Resonance in Medicine 16 (2008):p. 3152.
Blaimer, et al. 'Smash, Sense, Pills, Grappa, How to Choose the Optimal Method'. Top Magan Reson Imaging, vol. 15, No. 4, Aug. 2004, pp. 223-236.
Buchanan, Roger 'Cobalt on the way out' British Medical Journal, vol. 292, Feb. 1, 1986. p. 290.
Candes, et al. 'Robust Uncertainty Principles: Exact Signal Reconstruction from Highly Incomplete Frequency Information.' IEEE Transactions on Information Theory, vol. 52, No. 2, Feb. 2006, pp. 489-509.
Candes, et al. 'Sparsity and Incoherence in Compressive Sampling'. Electrical and Computer Engineering, Georgia Tech, Atlanta, GA, 90332. Nov. 2006, pp. 1-20.
Chng, N. et al. 'Development of inverse planning and limited angle CT reconstruction for cobalt-60 tomotherapy' Proceedings of 51st Annual Meeting of Canadian Organization of Medical Physicists and the Canadian College of Physicists in Medicine, 2005, McMaster University, Hamilton Ontario. Medical Physics, 2005, p. 2426. (4 pages).
CIPRA 'L1-magic' from SIAM News, vol. 39, No. 9, Nov. 2006. (3 pages).
Cosmus, Thomas C. et al.; "Advances in Whole-Body MRI Magnets"; IEEE/CSC & ESAS European Superconductivity New Forum (ESNF), No. 14; Oct. 2010; 6 Pages; The published version of this manuscript appeared in IEEE Transactions on Applied Superconductivity 21, Issue 3; pp. 2104-2109 (2011).
De Poorter J. et al. 'Noninvasive MRI Thermometry with the Proton Resonance Frequencey (PRF) Method: In Vivo Results in Human Muscle,' Magnetic Resonance in Medicine, Academic Press, Duluth, vol. 33, No. 1, Jan. 1995 pp. 74-81 XP000482971.
Donoho, David L., 'Compressed Sensing'. Department of Statistics, Stanford University. Sep. 14, 2004. (34 pages).
EP App. No. 10195476.6; Extended EP Search Report dated Jul. 4, 2011; 11 pages.
EP App. No. 10800553.9; Extended EP Search Report dated Oct. 17, 2013; 10 pages.
EP App. No. 17000760.3; Extended EP Search Report dated Nov. 9, 2017; 7 pages.
EU Office Action in app. 17734947.9, dated Oct. 14, 2021.
Extended European Search Report and supplementary European Search Opinion of European Patent application No. EP 10822326. 2-1560, dated Aug. 2, 2013, 11 pages.
Extended European Search Report in European Patent Application No. EP11850577, dated Jul. 9, 2014. 8 pages.
Fofanov, Dr. Denis et al.; "Magentic Properties of Stainless Steels: Applications, Opportunities and New Developments"; https://steelmehdipour.net/wp-content/uploads/2017/02/Magnetic-properties-of-stainless-steels.pdf ; Webpage retrieved Feb. 2017; 13 Pages.
Foroosh, Hassan, et.al. 'Extension of Phase Correlation to Subpixel Registration.' IEEE Transactions on Image Processing, vol. 11, No. 3, 2002, pp. 188-200.
Gerganov G et al, 'Portal image registration using the phase correlation method', 2013 IEEE Nuclear Science Symposium and Medical Imaging Conference (2013 NSS/MIC), IEEE, (Oct. 27, 2013), doi:10.1109/NSSMIC.2013.6829306, pp. 1-3, XP032601397.
Goitein, Michael. 'Organ and Tumor Motion: An Overview.' Seminars in Radiation Oncology. vol. 14, No. 1 Jan. 2004: pp. 2-9.
Goldberg, S. Nahum; G. Scott Gazelle, and Peter R. Mueller. 'Thermal Ablation Therapy for Focal Malignancy: A Unified Approach to Underlying Principles, Techniques, and Diagnostic Imaging Guidance.' Amer. J. of Roentgenology, vol. 174, Feb. 2000 pp. 323-331 XP002431995.
Golen et al., "A comparison of two scoring systems for late radiation toxicity in patients after radiotherapy for head and neck cancer," Rep Pract Oncol Radiother, 2005; 10(4): 179-192.
Green et al. 'Split cylindrical gradient coil for combined PET-MR system.' Proc. Intl. Soc. Mag. Reson. Med. 16 (2008):352.

(56) References Cited

OTHER PUBLICATIONS

Haacke, Mark E. et al. 'Constrained reconstruction: A superresolution, optimal signal-to-noise alternative to the Fourier transform in magnetic resonance imaging.' Medical Physics, AIP, Melville, NY, US, vol. 16, No. 3, May 1, 1989 (May 1, 1989), pp. 388-397, XP000034068, ISSN: 0094-2405, DDI: 10.1118/1.596427.

Hajdok, George. 'An Investigation of Megavoltage Computed Tomography Using a Radioactive Cobalt-60 Gamma Ray Source for Radiation Therapy Treatment Verification.' Thesis. May 2002. 150 pages.

Hernando, D. et al. 'Interventional MRI with sparse sampling: an application of compressed sensing.' Proceedings of International Society for Magnetic Resonance in Medicine. 16 (2008):p. 1482.

Hicks, et al., 'Early FDG-PET imaging after radical radiotherapy for non-small-cell lung cancer: Inflammatory changes in normal tissues correlate with tumor response and do not confound therapeutic response evaluation', International Journal of Radiation: Oncology Biology Physics; [Publication // Division of Scientific and Technical Information, International Atomic Energy Agency, ISSN 0074-1876 ; 1196], Pergamon Press, USA, (Oct. 1, 2004), vol. 60, No. 2, doi: 10.1016/J.IJROBP.2004.03.036, ISSN 0360-3016, ISBN 978-92-0-107304-4, pp. 412-418, XP004582712.

Hong J et al, 'Interventional navigation for abdominal therapy based on simultaneous use of MRI and ultrasound', Medical and Biological Engineering and Computing, Springer, Heildelberg, DE, vol. 44, No. 12, doi:10.1007/S11517-006-0133-2, ISSN 0140-0118, (Nov. 11, 2006), pp. 1127-1134, (Nov. 11, 2006), XP001551805.

Hong Pan, et al., Review; New and Emerging Techniques for Mapping Brain Circuitry; (2011) 67 ESBRR 1-2 226-251.

International Preliminary Report on Patentability, International Applicaiton No. PCT/US2018/059245, International Filing Date Nov. 5, 2018, dated Nov. 26, 2020, 24 pages.

International Search Report and Written Opinion dated Apr. 13, 2012, for corresponding international application No. PCT/US2011/066605; 9 pages.

International Search Report of PCT/US2010/057650 dated Feb. 2, 2011, 2 pages.

International Search Report of the International Searching Authority issued in International Application No. PCT/US2014/028792, dated Jul. 2, 2014. 3 pages.

Irarrazabal, Pablo, and Dwight G. Nishimura. 'Fast Three Dimensional Magnetic Resonance Imaging.' Magnetic Resonance in Medicine, vol. 33, No. 5, 1995, pp. 656-662.

Jaffray, David A., et al. 'Flat-Panel Cone Beam Computed Tomography for Image-Guided Radiation Therapy' Int. J. Radiation Oncology Biol. Phys., vol. 53, No. 5, pp. 1337-1349, Apr. 3, 2002, Elsevier Science Inc., USA.

Jan J. W. Lagendijk et al.; "MR Guidance in Radiotherapy", Physics in Medicine and Biology, Institute of Physics Publishing, Bristol GB, vol. 59, No. 21, Oct. 16, 2014, pp. R349-R369, XP020272054, ISSN: 0031-9155.

JP Office Action dated Jan. 11, 2022, Japanese Patent Application No. 2018-567083.

Jursinic, Paul et al. 'Characteristics of secondary electrons produced by 6, 10 and 24 MV x-ray beams' Phys. Med. Biol. 41 (1996) 1499-1509, United Kingdom.

Khan, Faiz M., 'The Physics of Radiation Therapy (second edition)', Lippincott Williams & Wilkins. Chapter 13. 1985. pp. 323-332.

Kwan-Jin Jung, et al., "Parallel Imaging with Asymmetric Acceleration to Reduce Gibbs Artifacts and to Increase Signal-To-Noise Ratio of the Gradient Echo Echo-Planar Imaging Sequence for Functional MRI," Magnetic Resonance in Medicine 67:419-427 (2012).

Lagendijk et al, 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061.

Lagendijk JJ W et al.: "MRI Guided Radiotherapy: A MRI based linear Accelerator", Radiotherapy and Oncology, vol. 56, No. 01, Sep. 21, 2000 (Sep. 21, 2000), pp. S60-S61.

Langen, K.M. et al. 'Organ Motion and its Management.' Int J. Radiation Oncology Biol. Phys., vol. 50, No. 1, pp. 265-278. 2001. Elsevier Science Inc., USA.

Law, C. , and Glover, G. 'Deconvolving Haemodynamic Response Function in fMRI under high noise by Compressive Sampling.' Proceedings of International Society for Magnetic Resonance in Medicine. 17 (2009):p. 1712. Stanford University, Stanford, CA, United States.

Li, Kang and Kanadae, Takeo. 'Nonnegative Mixed-Norm Preconditioning for Microscopy Image Segmentation.' Information Processing in Medical Imaging. Springer Berlin Heidelberg. vol. 5636. (2009):362-373.

Liang, J. and D. Yan. 'Reducing Uncertainties in Volumetric Image Based Deformable Organ Registration.' Medical Physics, vol. 30, No. 8, 2003, pp. 2116-2122.

Lopez, Hector Sanchez et al.; "Designing an Efficient Resistive Magnet for Magnetic Resonance Imaging"; IEEE Transactions on Magnetics, vol. 40, No. 5; Sep. 2004; pp. 3378-3381.

Lopez, Mike R. et al. 'Relativistic Magnetron Driven by a Microsecond E-Beam Accelerator with a Ceramic Insulator' IEEE Transactions on Plasma Science vol. 32, No. 3, Jun. 2004. pp. 1171-1180.

Lucas et al. 'Simultaneous PET-MR: toward a combined microPET. RTM.-MR system.' Proc. Intl. Soc. Mag. Reson. Med. 15(2007):922.

Lurie, D.J., PhD. 'Free radical imaging' The British Journal of Radiology. 74 (2001). pp. 782-784.

Lustig, et al. 'L1 SPIR-IT: Autocalibrating Parallel Imaging Compressed Sensing.' Electrical Engineering, Stanford University, Stanford, CA, United States. Radiology, Stanford University. Statistics, Stanford University (p. 334).

Lustig, M, et al. 'Faster Imaging with Randomly Perturbed, Undersampled Spirals and |L|_1 Reconstruction.' In: Proceedings of the 13th Annual Meeting of ISMRM, Miami Beach, 2005. (1 page).

Macura, Katarzyna J., Md, PhD. 'Advancements in Magnetic Resonance-Guided Robotic Interventions in the Prostate'. Top Magn Reson Imaging. vol. 19, No. 6. Dec. 2008. pp. 297-304.

Mah et al., "Measurement of intrafractional prostate motion using magnetic resonance imaging," Int. J. Radiation Oncology Boil. Phys. vol. 54, No. 2, pp. 568-575, 2002.

Mathieu Sarracanie et al: "Low Cost High Performance MRI", Proceedings of the International Society for Magnetic Resonance in Medicine, vol. 23, 702, May 15, 2015.

May et al., Abnormal Signal Intensity in Skeletal Muscle at MR Imaging: Patterns, Pearls, and Pitfalls, RadioGraphics 2000; 20: S295-S315.

McMahon et al., "Muscle Edema", AJR: 194, Apr. 2010, W284-W292.

Medtronic, Inc.. 'Image-Guided Surgery Overview'. 2010. 2 pages.

Meulenbroeks, David; "Aluminum versus Copper Conductors—Application of Aluminum Conductors in Bus Way Systems for more Sustainable Data Centers" ; Siemens Center of Competence Data Centers , The Netherlands; www.siemens.com/datacenter; White Paper Oct. 2014; 9 Pages.

Meyer, et al. "Fast Spiral Coronary Artery Imaging", Magnetic Resonance in Medicine 28, pp. 202-213 (1992).

Momy, A. et al al.; "Low-Leakage Wide-Access Magnet for MRI"; IEEE Transactions on Magnetics, vol. 33, No. 6; Nov. 1997; pp. 4572-4574.

Morgan, Patrick N. et al.; "Resistive Homogeneous MRI Magnet Design by Matrix Subset Selection"; Magnetic Resonance in Medicine 41:1221-1229; Wiley-Liss, Inc. (1999).

Mozer, Pierre C, Md, PhD. 'Robotic Image-Guided Needle Interventions of the Prostate'. Reviews in Urology. vol. 11, No. 1. 2009. pp. 7-15.

Muntener, Michael, MD et al. 'Transperineal Prostate Intervention: Robot for fully Automated MR Imaging-System Description and Proof of Principle in a Canine Model'. Radiology. vol. 247, No. 2. May 2008. pp. 543-549.

Mutic Sasa et al: "The ViewRay System: Magnetic Resonance-Guided and Controlled Radiotherapy", Seminars in Radiation Oncology, vol. 24, No. 3, Jun. 12, 2014 (Jun. 12, 2014), pp. 196-199.

Noel C et al: "TU-G-217A-09: Feasibility of Bowel Tracking Using Onboard Cine MRI for Gated Radiotherapy", Medical Physics, Jun.

(56) References Cited

OTHER PUBLICATIONS 28, 2012 (Jun. 28, 2012), pp. 1-2, XP55832625, Retrieved from the Internet: URL:https://aapm.onlinelibrary.wiley.com/doi/abs/10.1118/1.
Nomayr A et al.; 'MRI appearance of radiation-induced changes of normal cervical tissues', Eur Radiol., (2001), vol. 11, No. 9, doi:doi:10.1007/s003300000728, pp. 1807-1817, XP055095676.
Notice of Allowance dated Apr. 7, 2021 for U.S. Appl. No. 16/598,564 (pp. 1-5).
Notice of Allowance dated Aug. 27, 2020 for U.S. Appl. No. 16/116,187 (pp. 1-8).
Notice of Allowance dated Aug. 28, 2020 for U.S. Appl. No. 15/851,543 (pp. 1-7).
Notice of Allowance dated Feb. 26, 2020, for U.S. Appl. No. 15/436,620 (pp. 1-9).
Notice of Allowance dated Jul. 13, 2018 for U.S. Appl. No. 14/550,464 (pp. 1-11).
Office Action (Notice of Allowance and Fees Due (PTOL-85)) dated Aug. 25, 2021 for U.S. Appl. No. 16/179,764 (pp. 1-8).
Office Action dated Apr. 1, 2021 for U.S. Appl. No. 15/630,890 (pp. 1-19).
Office Action dated Feb. 18, 2020 for U.S. Appl. No. 16/179,764 (pp. 1-10).
Office Action dated Jan. 5, 2018 for U.S. Appl. No. 14/550,464 (pp. 1-21).
Office Action dated Jul. 17, 2020 for U.S. Appl. No. 15/851,543 (pp. 1-7).
Office Action dated Jul. 17, 2020 for U.S. Appl. No. 16/116,187 (pp. 1-7).
Office Action dated Jul. 24, 2020 for U.S. Appl. No. 15/630,890 (pp. 1-10).
Office Action dated Jun. 11, 2020 for U.S. Appl. No. 16/195,673 (pp. 1-14).
Office Action dated Mar. 9, 2020 for U.S. Appl. No. 16/204,838 (pp. 1-13).
Office Action dated Mar. 20, 2020, for U.S. Appl. No. 16/195,673 (pp. 1-12).
Office Action dated Mar. 22, 2018 for U.S. Appl. No. 14/550,464 (pp. 1-22).
Office Action dated May 14, 2021 for U.S. Appl. No. 16/179,764 (pp. 1-9).
Office Action dated Nov. 4, 2020 for U.S. Appl. No. 16/179,764 (pp. 1-8).
Office Action dated Sep. 8, 2020 for U.S. Appl. No. 16/204,838 (pp. 1-17).
Office Action dated Nov. 13, 2020 for U.S. Appl. No. 16/598,564 (pp. 1-9).
Overweg et al. 'System for MRI guided Radiotherapy.' Proc. Intl. Soc. Mag. Reson. Med. 17(2009):594.
Overweg, Johan; "MRI Main Field Magnets"; Philips Research; Hamburg, Germany; 7 Pages.
Partial International Search Report Issued in International Application No. PCT/US2013/039009, dated Oct. 18, 2013. 2 pages.
Pasternak et al., Free Water Elimination and Mapping from Diffusion, Magnetic Resonance in Medicine 62:717-730, 2009.
Patriciu, Alexandru, et al., 'Automatic Brachytherapy Seed Placement Under MRI Guidance'. IEEE Transactions on Biomedical Engineering. vol. 54, No. 8. Aug. 2007. pp. 1-8.
PCT App. No. PCT/US2010/039036; International Search Report dated Aug. 11, 2010; (pp. 1-2).
PCT App. No. PCT/US2010/042156; International Search Report and Written Opinion dated Sep. 10, 2010 ; 15 pages.
PCT App. No. PCT/US2016/063416; International Preliminary Report on Patentability and International Search Report with Written Option dated Jun. 7, 2018; 9 pages.
PCT App. No. PCT/US2017/020015; International Search Report and Written Opinion dated Jul. 26, 2017; 18 pages.
PCT App. No. PCT/US2017/038867; International Search Report and Written Opinion dated Nov. 8, 2017; (pp. 1-12).
Pryor, Larry et a.: "A Comparison of Aluminum vs. Copper Used in Electrical Equipment"; 7 Pages.
Raaijmakers, A.J.E et al. 'Integrating a MRI scanner with a 6 MV radiotherapy accelerator: dose increase at tissue-air interfaces in a lateral magnetic field due to returning electrons.' Phys. Med. Biol. 50 (2005) pp. 1363-1376.
Raaymakers, B.W et al. 'Integrating a MRI scanner with a 6 MV radiotherapy accelerator: dose deposition in a transverse magnetic field', Phys. Med. Biol. 49 (2004) 4109-4118.
Rancati et al., NTCP Modeling of Subacute/Late Laryngeal Edema Scored by Fiberoptic Examination, Int. J. Radiation Oncology Biol. Rhys., vol. 75, No. 3, pp. 915-923, 2009.
Reddy, B. Srinivasa, and B. N. Chatterji. 'An FFT-Based Technique for Translation, Rotation, and Scale-Invariant Image Registration.' IEEE Transactions on Image Processing, vol. 5, No. 8, Aug. 1996, pp. 1266-1271.
Riek, et al. "Flow Compensation in MRI Using a Phase-Corrected Real Reconstruction", Magnetic Resonance in Medicine 30, pp. 724-731, 1993.
Roullot Elodie et al. 'Regularized reconstruction of 3D high-resolution magnetic resonance images from acquisitions of anisotropically degraded resolutions.' Pattern Recognition, 2000. Proceedings. 15th International Conference on Sep. 3-7, 2000; [Proceedings of the International Conference on Pattern Recognition. (ICPR)], Los Alamitos, CA, USA, IEEE Comput. Soc, US, vol. 3, Sep. 3, 2000 (Sep. 3, 2000), pp. 346-349.
Sanchez, H et al.; "Approach to Design an Efficient Resistive Magnet for MRI"; Proc. Intl. Soc. Mag, Reson. Med. 11 (2003); p. 2409.
Sanguineti et al., Dosimetric Predictors of Laryngeal Edema, Int. J. Radiation Oncology Biol. Phys., vol. 68, No. 3, pp. 741-749, 2007.
Schreiner, John; Kerr, Andrew; Salomons, Greg; Dyck, Christine, and Hajdok, George, 'The Potential for Image Guided Radiation Therapy with Cobalt-60 Tomotherapy', MICCAI 2003, LNCS 2879, pp. 449-456, 2003.
Schreiner, L. John, et al. 'The role of Cobalt-60 in modern radiation therapy: Dose delivery and image guidance'. Journal of Medical Physics, vol. 34, No. 3, 2009, 133-136.
Sempau, Josep et al. 'DPM, a fast, accurate Monte Carlo code optimized for photon and electron radiotherapy treatment planning dose calculations.' Phys. Med. Biol. 45 (2000) pp. 2263-2291, Received Feb. 29, 2000. Printed in the UK.
Sherouse, George W. et al. 'Virtual Simulation in the Clinical Setting: Some Practical Considerations', Int. J. Radiation Oncology Biol. Phys. vol. 19, pp. 1059-1065, Apr. 26, 1990, Pergamon Press, USA.
Shvartsman et al. 'Gradient Coil Induced Eddy Current Computation Using the Boundary Elements Method.' Proc. Intl. Soc. Mag. Reson. Med. 17(2009):3055.
St. Aubin et al.,, 'Magnetic decoupling on the linac in a low field biplanar linac-MR system', Med. Phys, 37 (9), Sep. 2010, pp. 4755-4761.
Stoianovici, Dan, et al. MRI Stealth Robot for Prostate Interventions. Minimally Invasive Therapy. 2007. pp. 241-248.
Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.
Tokuda, J. et al. 'Real-Time Organ Motion Tracking and Fast Image Registration System for MRI-Guided Surgery.' Systems and Computers in Japan Scripta Technica USA. vol. 37, No. 1. Jan. 2006: 83-92. Database Inspec [Online]. The Institution of Electrical Engineers, Stevenage, GB; Jan. 2006.
Tokuda, Junichi; Morikawa, Shigehiro; Dohi, Takeyoshi; Hata, Nobuhiko; Motion Tracking in MR-Guided Liver Therapy by Using Navigator Echoes and Projection Profile Matching, 2004. vol. 11. No. 1. pp. 111-120.
Trzasko et al. 'Highly Undersampled Magnetic Resonance Image Reconstruction via Homotopic L0—Minimization' IEEE Transactions on Medical Imaging. vol 28. No. 1. Jan. 31. 2009, pp. 106-121.
Wang et al., Evolution of Radiation-Induced Brain Injury: MRI Imaging—Based Study, Radiology: vol. 254: No. 1; Jan. 2010.

(56) References Cited

OTHER PUBLICATIONS

Warrington, Jim et al. 'Cobalt 60 Teletherapy for Cancer: A Revived Treatment Modality for the 21st Century', 2002 The Institution of Electrical Engineers, pp. 19-1-19/19.
Wazer, David E. et al. 'Principles and Practice of Radiation Oncology (fifth edition).', Wolters Kluwer/ Lippincott Williams & Wilkins. 2008. 2 pages.
Weaver, John B.; "Simultaneous Multislice Acquisition of MR Images", Magnetic Resonance in Medicine, John Wiley & Sons, Inc., vol. 8, No. 3, Nov. 1, 1988, pp. 275-284, XP000003030, ISSN: 0740-3194.
Webb, S. 'The physical basis of IMRT and inverse planning' The British Journal of Radiology, 76 (2003), 678-689, 2003 The British Institute of Radiology.
Webb, Steve, 'Intensity-modulated radiation therapy using only jaws and a mask: II. A simplified concept of relocatable single-bixel attenuators', published May 22, 2002, Institute of Physics Publishing, Physics in Medicine and Biology, Phys. Med. Biol. 47 (2002) 1869-1879.
Webb, Steve. "Historical Perspective on IMRT." Institute of Cancer Research and Royal Marsden NHS Trust. 2002. (23 pages).
Yang, Junfeng, et al. 'A Fast TVL1-L2 Minimization Algorithm for Signal Reconstruction from Rartial Fourier Data.' Technical Report, TR08-27, CAAM, Rice University Houston, TX, 2008. pp. 1-10.
Zaitsev M et al.: "Shared k-space Echo Planar Imaging with Keyhole," Magnetic Resonance in Medicine, John Wiley & Sons, Inc. US, vol. 45, Jan. 1, 2001, pp. 109-117, XP002311925, ISSN: 0740-3194.
Zitova B et al, 'Image Registration Methods: a Survey', Image and Vision Computing, Elsevier, Guildford, GB, (Oct. 1, 2003), vol. 21, No. 11, doi:10.1016/ S0262-8856(03)00137-9, ISSN 0262-8856, pp. 977-1000, XP001189327.

\* cited by examiner

When imaging:

When not imaging:

RESISTIVE ELECTROMAGNET SYSTEMS AND METHODS

RELATED APPLICATION(S)

This application is a continuation of U.S. application Ser. No. 16/179,764, filed Nov. 2, 2018, titled "Resistive Electromagnet Systems and Methods," now U.S. Pat. No. 11,209,509, which claims priority to and the benefit of U.S. Provisional Application No. 62/672,525, filed May 16, 2018, titled "Resistive Electromagnet Systems and Methods," and U.S. Provisional Application No. 62/677,546, filed May 29, 2018, titled "Resistive Electromagnet Design and Construction," the contents of each are hereby incorporated by reference in their entirety.

BACKGROUND

Magnetic resonance imaging (MRI), or nuclear magnetic resonance imaging, is a noninvasive imaging technique that uses the interaction between radio frequency pulses, a strong magnetic field (modified with weak gradient fields applied across it to localize and encode or decode phases and frequencies) and body tissue to obtain projections, spectral signals, and images of planes or volumes from within a patient's body. Magnetic resonance imaging is particularly helpful in the imaging of soft tissues and may be used for the diagnosis of disease. Real-time or cine MRI may be used for the diagnosis of medical conditions requiring the imaging of moving structures within a patient. Real-time MRI may also be used in conjunction with interventional procedures, such as radiation therapy or image guided surgery, and also in planning for such procedures.

SUMMARY

Electromagnet designs are disclosed that may be utilized in magnetic resonance imaging systems. Certain embodiments may comprise a resistive, solenoidal electromagnet for whole-body MRI including conductors and ferromagnetic material within an envelope of the electromagnet. The electromagnet may be gapped and the ferromagnetic material may be steel. In some variations, the electromagnet may be configured for current flow in only one circumferential direction within the electromagnet.

The electromagnet may be configured as resistive, solenoidal electromagnet for whole-body MRI having a field strength of at least 0.05 Tesla comprising conductors for creating a main electromagnetic field of the electromagnet, where the main electromagnetic field is not generated by bundles of conductors. In some variations, the main electromagnetic field may be generated by layers of conductors (for example, less than 10 layers).

Electromagnet designs disclosed herein may utilize non-metallic formers for supporting conductors such as fiberglass formers. The layers of conductors and the non-metallic formers can be constructed to form a rigid object by fixing them together with an epoxy. The electromagnet can have two halves and the two halves can be held apart by a fixation structure, which may be made from carbon fiber. In one embodiment, conductors may be utilized that have a cross-sectional area greater than 0.5 centimeters squared.

In another embodiment, the magnetic resonance imaging system may include a resistive, solenoidal electromagnet for whole-body MRI having a field strength of at least 0.05 Tesla with conductors for creating a main electromagnetic field of the electromagnet that cover at least 50% of the envelope of the electromagnet.

In certain systems disclosed herein, the power supply for powering the resistive electromagnet can have more than one part per ten thousand current fluctuation at frequencies of 180 Hz or above and may not include a current filter separate from filtering provided by the resistive electromagnet itself. The power supply may also be a single channel power supply and may not include active current controls. In certain embodiments, the system can include a battery, where the resistive electromagnet can be connected to the battery and the system can be configured so that the battery can be charged by the power supply. The system can also include a fuel cell, where the system can be configured so that the fuel cell is located between the power supply and the resistive electromagnet.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

The present disclosure relates to technologies that may be utilized in various systems, devices, methods and computer software used with electromagnets. Certain embodiments of the technologies described herein may be beneficially employed in conjunction with magnets used for magnetic resonance imaging (MRI), although it is contemplated that these technologies may also be implemented in electromagnets for other applications.

One particular type of MRI magnet discussed herein as benefiting from these technologies is a solenoidal (i.e., cylindrical), resistive electromagnet (to be distinguished from, e.g., permanent magnets, superconducting electromagnets and non-solenoidal electromagnets such as dipolar electromagnets). When the term solenoid or solenoidal is used herein to describe a magnet, such refers merely to the so-named configuration of certain MRIs (i.e., cylindrical); it is not by any means limited to magnet configurations that might typically be described as a perfect solenoid (e.g., a single helically wound conductor). While these technologies herein can be used in any size MRI electromagnet, the main implementations discussed herein relate to magnets for whole-body MRI systems. When the term "whole-body" is used herein, it refers to typical size magnetic resonance imaging systems (e.g., the Siemens Healthineers Magnetom Aera and the GE Signa), instead of small MRIs for imaging particular body parts (such as the Esaote O-Scan), or those for veterinary applications, research, etc.

In the case of whole-body MRI electromagnets, is contemplated that the technologies herein can be used at any MRI field strength, although imaging may suffer below 0.05 Tesla and power requirements can be high for resistive electromagnets above 0.5 Tesla. Two particular implementations for resistive, solenoidal electromagnets discussed herein have field strengths of 0.12 T and 0.2 T.

Figure 1:
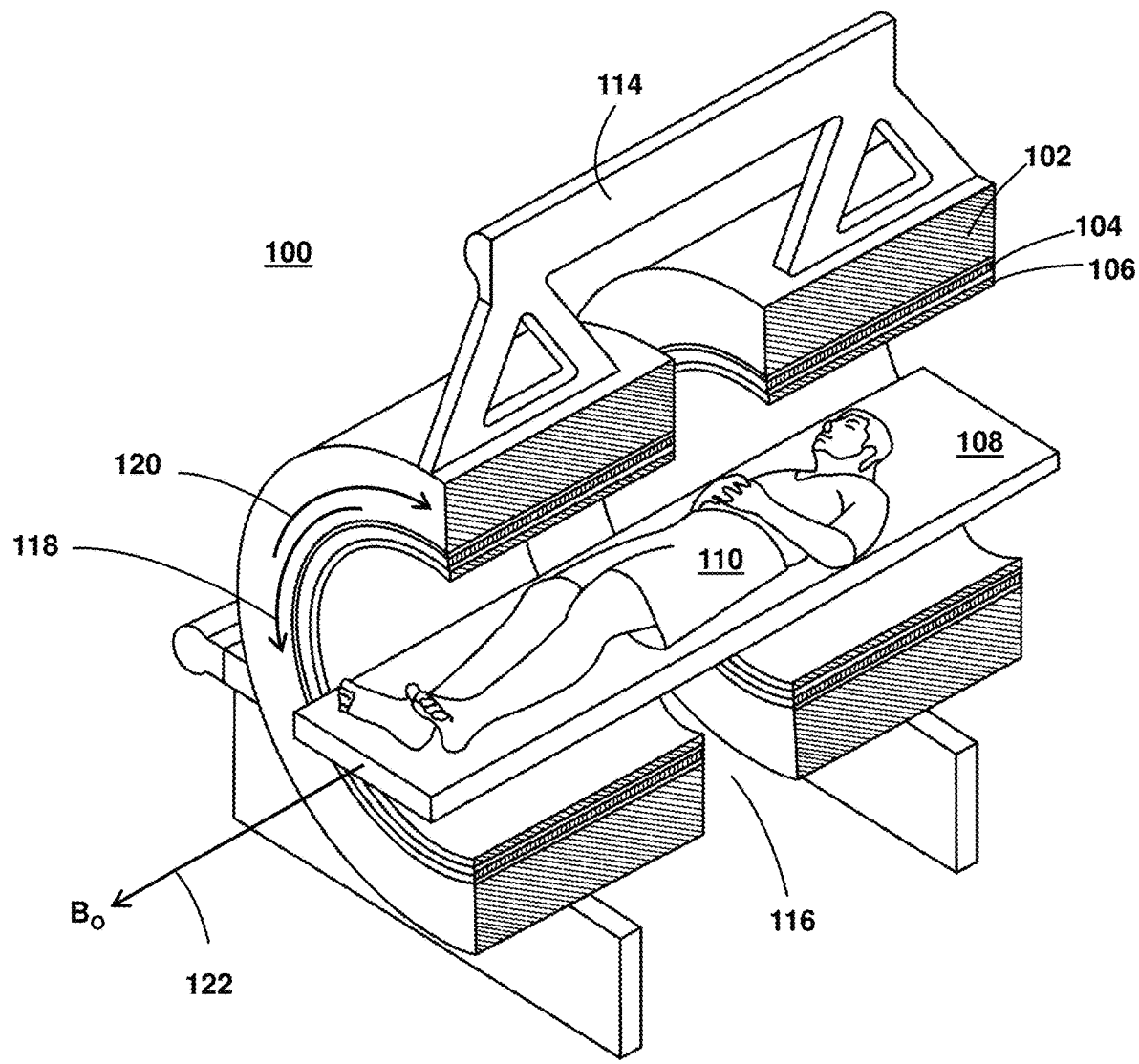
FIG. 1 is a diagram illustrating a simplified perspective view of an exemplary magnetic resonance imaging system in accordance with certain aspects of the present disclosure.
Figure 5:
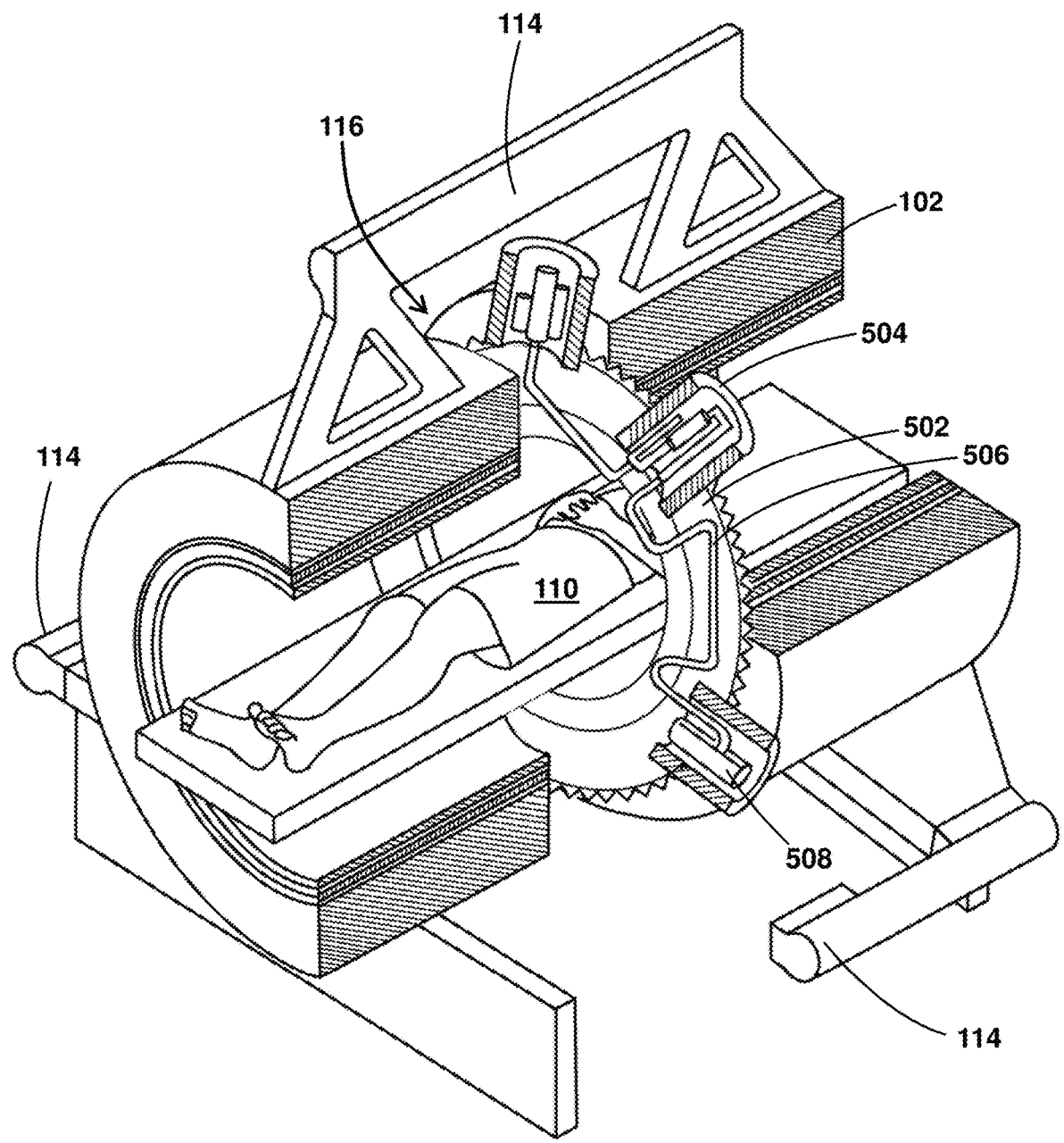
FIG. 5 is a diagram illustrating a simplified perspective view of an exemplary magnetic resonance imaging system incorporating an exemplary interventional device for radiation therapy in accordance with certain aspects of the present disclosure.

The technologies of the present disclosure can be used in traditional solenoidal MRI systems used for diagnostic purposes, but can be particularly beneficial in gapped solenoidal systems, such as the system depicted in FIG. 1. When the present disclosure refers to "gapped" magnets, such is intended to include solenoidal electromagnets having a gap (as in FIG. 1), as opposed to dipolar magnet arrangements, often referred to as "open" MRI systems. Gapped systems, such as those discussed herein, may be useful for interventional applications such as MRI-guided radiotherapy, MRI-guided surgery, and the like. An example of such a radiotherapy system is depicted in FIG. 5, which shows a gantry in the gap having magnetic shielding structures mounted thereon that contain components of a linear accelerator.

While the technologies described herein are predominantly applied to electromagnets as used with MRI, these features may also be used with suitable magnet designs, regardless of purpose. For example, more general magnet systems can include those used in research, industry, or practical applications such as magnetic switching, motors, power generators, relays, speakers, magnetic separation equipment, etc.

FIG. 1 illustrates one implementation of a magnetic resonance imaging system (MRI) 100 consistent with certain aspects of the present disclosure. In FIG. 1, the MRI 100 includes a main electromagnet 102, a gradient coil assembly 104 and an RF coil system 106. Within MRI 100 is a patient couch 108 on which a human patient 110 may lie.

The main electromagnet 102 of MRI 100 may be a gapped solenoidal electromagnet separated by buttresses 114 with a gap 116 as shown in FIG. 1. A "gap," as the term is used herein, refers to the type of solenoidal magnet gap 116 depicted in FIGS. 1 and 2; it does not refer to the open space in a dipolar magnet arrangement where the patient is positioned for imaging. In one implementation considered herein, gap 116 shown in FIG. 1 is 28 cm.

Gradient coil assembly 104 contains the coils necessary to add small varying magnetic fields on top of the field of main electromagnet 102 to allow for spatial encoding of the imaging data. Gradient coil assembly 104 may be a continuous cylindrical assembly, a split gradient coil assembly as shown in FIG. 1, or other designs as may be necessary for the particular MRI configuration utilized.

RF coil system 106 is responsible for exciting the spins of hydrogen protons within patient 110 and for receiving subsequent signals emitted from patient 110. RF coil system 106 thus includes an RF transmitter portion and an RF receive portion. The implementation in FIG. 1 includes a singular body coil performing both the RF transmit and RF functionalities. RF coil system 106 may alternatively divide transmit and receive functionalities between a body coil and a surface coil, or may provide both transmit and receive functionalities within a surface coil.

Magnetic resonance imaging systems include control systems configured for the acquisition and processing of magnetic resonance imaging data from patient 110, including image reconstruction. Such control systems may contain numerous subsystems, for example, those which control operation of the gradient coil assembly 104, the RF coil system 106, portions of those systems themselves, and those that process data received from RF coil system 106 and perform image reconstruction. Additional control system functionality can be included, for example, when an interventional device (such as a radiation therapy device) is integrated with MRI 100.

Figure 2:
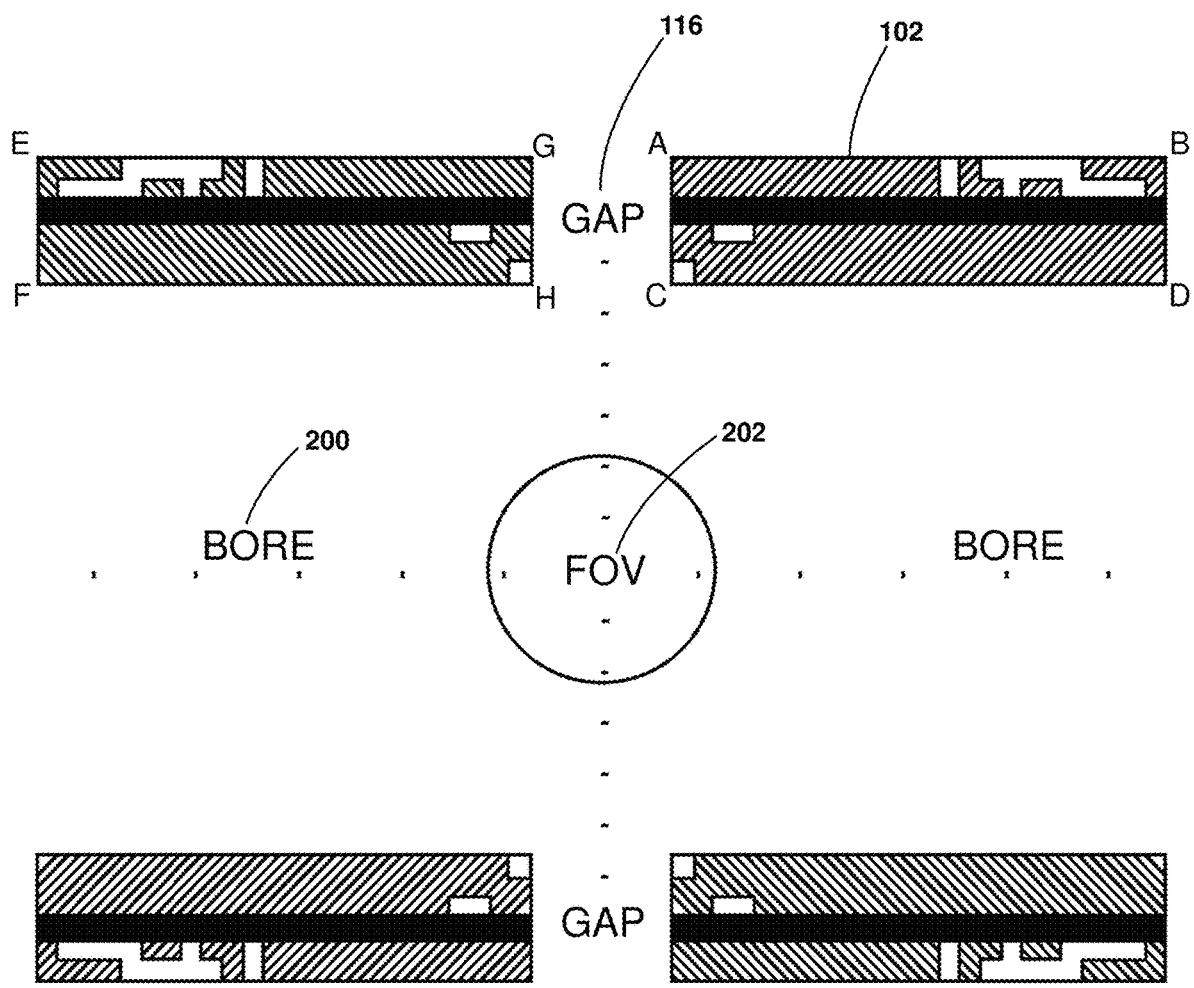
FIG. 2 is a diagram illustrating a simplified sectional view of an exemplary electromagnet for generating the main magnetic field for a gapped solenoidal magnet, as shown in FIG. 1.

FIG. 2 illustrates a simplified cross-section of the main electromagnet 102 shown in FIG. 1, including a gap 116. Gradient coil 104 and RF coil 106 are not depicted in this figure. All four visible cross sections of main electromagnet 102 are shown in FIG. 2, surrounding the MRI 100's bore 200 and the imaging area or Field Of View 202.

FIG. 2 illustrates an important concept that will be referred to throughout this disclosure, specifically, a "magnet envelope." The concept of a magnet envelope, as the term is used herein, may be demonstrated by reference to the letters A, B, C and D in FIG. 2. The term refers to the outer boundaries of conductors used to generate the electromagnet's main magnetic field. In cases where the outer boundary of the magnet's conductors is not a rectangular shape, the magnet envelope is understood to mean the smallest rectangle (or tightly fitting convex polygon, for irregular shapes) that can be used to encompass the conductors. For example, no conductor is used in electromagnet 102 near the corner labeled "C" but the magnet envelope, rather than following the exact boundary of the conductors, extends all the way to corner "C" to form a rectangle. While the magnet envelope is depicted in the figures in two-dimensional cross-section, it is understood that the magnet envelope actually encompasses the entire three-dimensional volume corresponding to the cross-section(s) (i.e., generally, the volumetric area defined by sweeping the cross-section around the solenoidal magnet's Z-axis at a constant radius).

In a gapped magnet, as shown in FIG. 2, "within the magnet envelope" means within the magnet envelope created by the conductors in both halves of the magnet. In the example illustrated in FIG. 2, the magnet envelope is understood to encompass the area bounded by points A, B, C, D and also the area bounded by points E, G, F, H, but it does not include the area within magnet gap 116. If the electromagnet of FIG. 2 was a non-gapped design, the magnet envelope would be defined by the letters E, B, F, and D.

Figure 3:
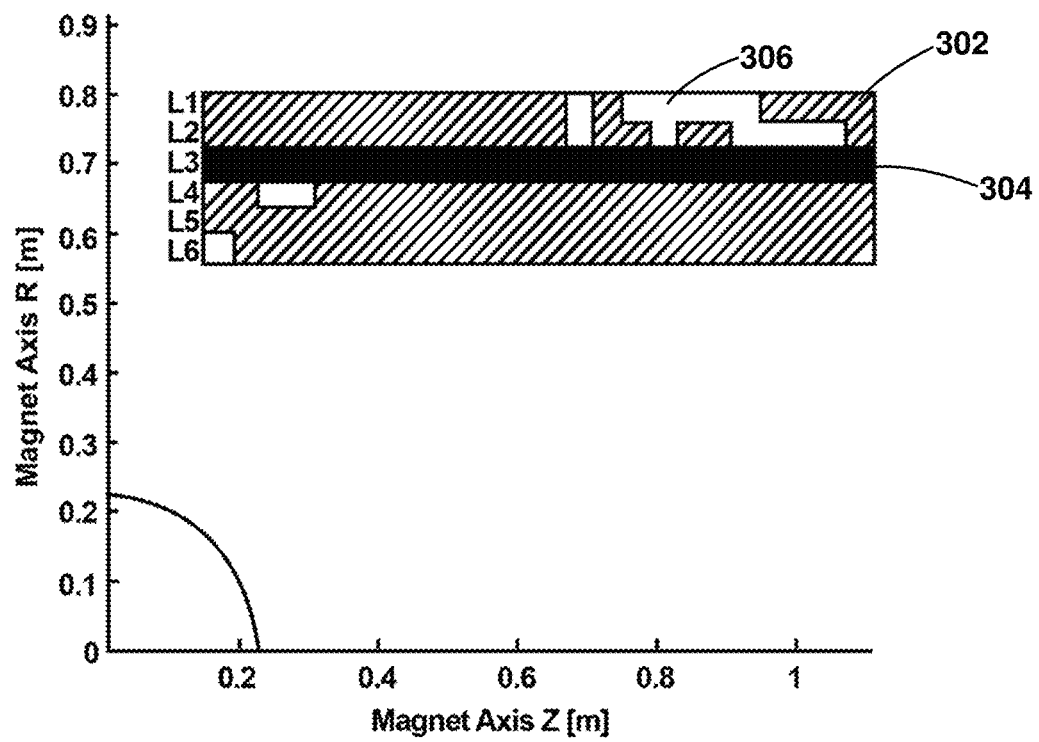
FIG. 3 is a diagram illustrating a simplified sectional view and a simplified perspective view of layers of an electromagnet in accordance with certain aspects of the present disclosure.
Figure 3:
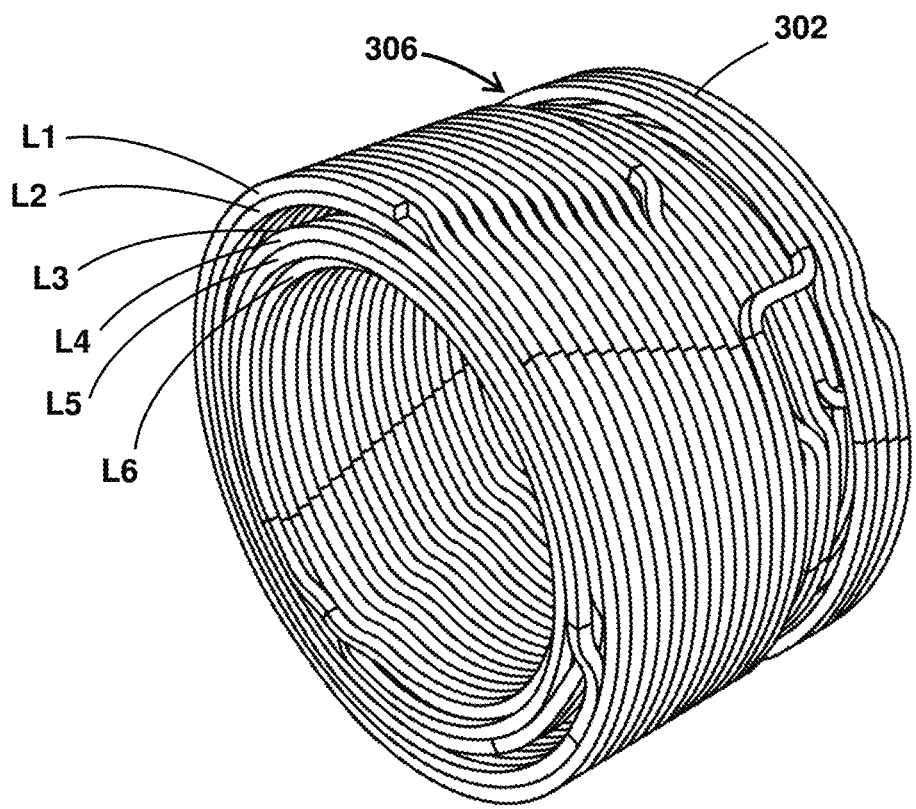

FIG. 3 focuses in on the right half of electromagnet 102 that is shown in FIGS. 1 and 2, and specifically the upper right quadrant of FIG. 2. This figure adds dimensions to the exemplary implementation to show, on the x-axis, distances from the central field of view along the magnet's Z-axis and, on the Y-axis, radial distances from the solenoidal magnet's Z-axis.

In the exemplary design of FIG. 3, conductors 302 are represented by cross-hatched areas, ferromagnetic material 304 is represented by solid black areas, and the absence of conductors or ferromagnetic material is designated by whitespace 306.

Electromagnets are, of course, made with conductors, for example, loops of copper wire. As used herein, the term "conductors" refers to any conductive loops, coils or other structures that are used to generate the main magnetic field of an electromagnet. When the plural form of the word is used herein, it is intended to cover not only a plurality of conductors (e.g., separate coils or bundles of wire), but plural "conductors" may also refer to structures that are technically one continuous conductor but may comprise, for example, multiple conductive loops, turns or other structures.

One particular beneficial implementation of the present disclosure has ferromagnetic material included within the envelope of the electromagnet. An example of such is shown in FIG. 3 as ferromagnetic material 304 and may include materials such as iron, steel alloys and even a martensitic stainless steel (but not a lower-permeability austenitic stainless steel). For example, ferromagnetic materials with initial relative permeabilities above 20 can be used. Although ferromagnetic materials with low initial relative permeabilities such as martensitic and ferritic stainless steel are acceptable, it is preferable to utilize materials with higher initial relative permeabilities, such as non-stainless steels (e.g., SAE1006 steel).

FIG. 3 illustrates one particular implementation that includes ferromagnetic material within an envelope of an electromagnet. This particular magnet configuration includes six layers, which are labeled on the top and bottom of FIG. 3 as L1, L2, L3, L4, L5 and L6. Layers can be understood to mean sections of the electromagnet that are located at a given radial distance from the magnet axis. In the example of FIG. 3, layers L1 through L6 have each been designed to be 4 cm tall. This example thus includes 4 cm×4 cm conductors wrapped in a generally cylindrical shape at layers L1, L2, L4, L5 and L6, and a generally cylindrical piece of 4 cm thick ferromagnetic material (e.g., steel) at L4 (the ferromagnetic material is not depicted in the bottom half of FIG. 3).

While the example of FIG. 3 utilizes relatively large and evenly spread out conductors, the beneficial technologies described herein can also be utilized in electromagnet designs that include "bundles" of conductors. For example, ferromagnetic material within the envelope can be beneficial for an electromagnet designed with, for example, 10 bundles of smaller conductors wrapped together and placed at particular locations within the magnet to generate the desired magnetic field.

The present disclosure contemplates that the layers of an electromagnet design similar to that of FIG. 3 do not need to all be the same height, and the height of a ferromagnetic material layer does not need to be the same height as any of the conductor layers. For example, in one embodiment, the conductor layers are 4 cm tall, while the ferromagnetic layer is only 2 cm tall.

The present disclosure contemplates many different configurations of ferromagnetic material within the envelope of electromagnet. While the example of FIG. 3 includes a single and complete layer of ferromagnetic material, electromagnets may similarly be designed with more than one layer of ferromagnetic material, or partial layer(s) of ferromagnetic material. While the examples discussed thus far contemplate cylindrically-shaped ferromagnetic material layers, it is contemplated that ferromagnetic materials within the electromagnet envelope need not be cylindrical in shape. Furthermore, if a portion of a ferromagnetic element is located within the envelope, and a portion of it extends out of the envelope, such a design is contemplated to meet the "ferromagnetic material within the envelope" construct because a portion is still within the envelope and will provide the beneficial results sought. Stated another way, if the ferromagnetic material depicted at layer 3 of FIG. 3 extended further out along magnet axis Z, beyond the envelope that is defined by the conductors, such an implementation would still be understood herein as having ferromagnetic material "within the envelope" of the electromagnet.

The present disclosure specifically contemplates its technologies being utilized in magnet designs that have no yoke and magnet designs that have no flux return. The "ferromagnetic material within the electromagnet envelope" magnet designs discussed herein are distinguishable from flux returns and yokes. For example, for a solenoidal magnet (as illustrated in FIG. 2), a flux return or yoke would be positioned within the bore 200 of the magnet, rather than "within the envelope" of the magnet (as delineated by the letters A, B, C, D, E, F, G, H described previously). Similarly, dipole magnet designs that commonly utilize flux returns or yokes are likewise distinguishable from the designs of the present disclosure.

The present disclosure also specifically distinguishes magnets where the main magnetic field is generated primarily by a permanent magnet or magnets. While such systems may seem to include ferromagnetic material within their magnet's envelope, they are distinct from the technologies disclosed herein, which relate to electromagnets and define "within the envelope" as within the envelope of conductors used to generate the electromagnet's main magnetic field.

In an exemplary design, depicted in FIG. 3, it can be seen that the amount of ferromagnetic material is approximately one sixth the volume of the overall electromagnet or approximately one fifth the volume of the conductors. In another implementation, the height of the ferromagnetic layer may be cut in half, and the overall volume of ferromagnetic material decreased to only about one tenth the volume of the conductors. In other implementations, the volume of the ferromagnetic material may be as small as one twentieth the volume of the conductors. In particular, the volume and configuration of ferromagnetic materials can vary greatly, and can be determined through modeling particular magnet designs with software such as Comsol MultiPhysics or Faraday (by Integrated Engineering Solutions, Inc.) to arrive at configurations resulting in magnetization currents within the ferromagnetic materials sufficient to improve the main magnetic field homogeneity without requiring additional power (for example, to drive negative current loops).

Figure 4:
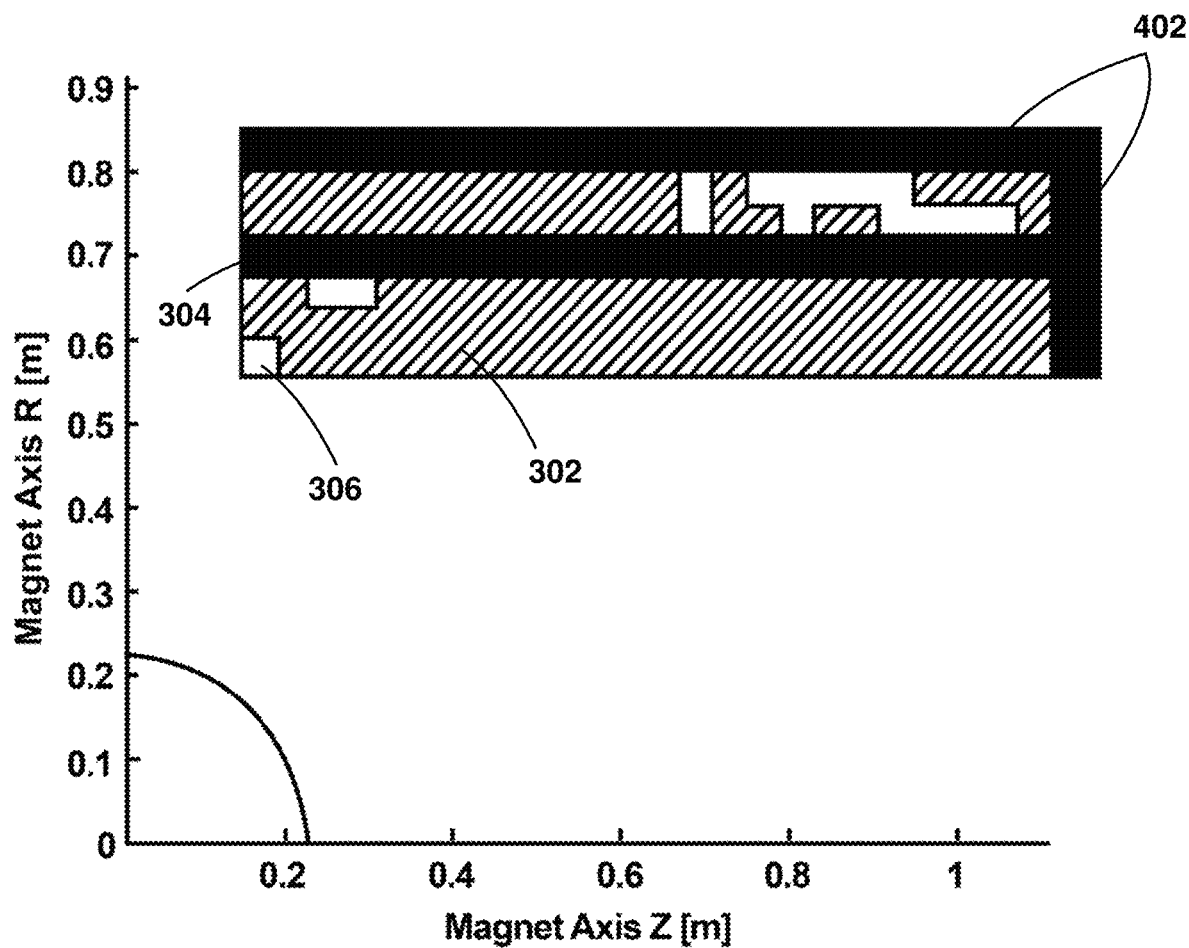
FIG. 4 is a diagram illustrating a simplified sectional view of an electromagnet that includes additional ferromagnetic material for reducing fringe fields in accordance with certain aspects of the present disclosure.

It should be noted that the electromagnet designs contemplated herein may include additional ferromagnetic materials outside the envelope of the electromagnet, which are configured to reduce the fringe field of the electromagnet. An example of such fringe field reducing material 402 is illustrated in FIG. 4. For example, this additional ferromagnetic material 402 may be designed as an L-shaped cross-section steel structure that is 1-2 cm thick. When such additional passive shielding is included in a design, it should be taken into account in the magnet modeling described above, along with the conductors and the ferromagnetic materials within the envelope of the electromagnet.

It should also be noted that when an electromagnet is being utilized in conjunction with an interventional application that may require placement of ferromagnetic materials in or near the magnet, modeling for design and optimal homogeneity should take into account such materials as well. FIG. 5 depicts such an interventional application, specifically, an MRI-guided radiation therapy system. In addition to the electromagnet 102, FIG. 5 depicts a gantry 502 on which magnetic shielding shells 504 are mounted in order to protect portions of a linear accelerator 508 from the electromagnet's main magnetic field. As depicted, the linear accelerator portions 508 may be connected utilizing RF waveguides 506. In such an exemplary design, the magnetic shielding shells 504 include large amounts of ferromagnetic material that should also be taken into account when designing the electromagnet, along with the conductors and the ferromagnetic materials included within the envelope of the electromagnet.

One embodiment of the present disclosure made thus be a magnetic resonance imaging (MRI) system including a resistive, solenoidal electromagnet for whole-body MRI including conductors and ferromagnetic material within an envelope of the electromagnet. The electromagnet may be gapped and the ferromagnetic material may comprise steel. In different embodiments, the volume of ferromagnetic material may be at least one sixth the volume of the conductors or at least one twentieth the volume of the conductors. In certain designs, the electromagnet may comprise a plurality of cylindrical layers and the ferromagnetic material may comprise a layer of the plurality of cylindrical layers. Alternatively, the ferromagnetic material may comprise a portion of a layer of the plurality of cylindrical layers. In still other embodiments, the ferromagnetic material may comprise a plurality of layers or a plurality of portions of layers of the plurality of cylindrical layers.

Many existing magnet designs, especially those for gapped solenoidal magnets, require currents within the electromagnet to flow in a positive direction and also in a negative direction in order to attain the desired homogeneity of the magnetic field. As used herein, a "positive" current flow is a flow direction that contributes positively to a magnet's main magnetic field Bo (see, e.g., positive flow direction 118 and main magnetic field 122 in FIG. 1). A "negative" current flow opposes the magnet's main magnetic field Bo (see, e.g., negative flow direction 120 in FIG. 1). These circumferential flow patterns are easily understood in light of the right-hand rule of physics.

In electromagnets that rely on conductor bundles to create the main magnetic field, certain bundles may have positive current flows and other bundles may have negative current flows. Similarly, for the electromagnet design depicted at the bottom of FIG. 3, a number of the conductor S-bends incorporated therein could be exchanged for U-bends, causing current to flow in a negative direction.

Using the technologies of the present disclosure, for example, magnet designs including ferromagnetic material within the magnet envelope, allows for magnet designs containing only positive current flows to produce satisfactorily homogeneous fields, even in gapped magnet configurations.

In some implementations of the present disclosure, a magnetic resonance imaging system may thus comprise a resistive, solenoidal electromagnet for whole-body MRI including conductors and ferromagnetic material within an envelope of the electromagnet where the system may be gapped and the electromagnet may be configured for current flow in only one circumferential direction within the magnet. For example, each of the bundles driving the main magnetic field may have a positive current direction, or, in the case of a non-bundled design, each of the conductors (e.g., as depicted in the bottom of FIG. 3) is configured, bent or formed to provide for positive flow currents only.

In other embodiments, the electromagnet may be configured for less than 5% negative current flow or less than 10% negative current flow. For example, in the embodiment of FIG. 3, less than 5% or 10% of the conductors may be configured or formed in a manner to result in negative current flows. Stated another way, less than 5% or 10% of the current loops are configured for negative flows (e.g., a loop representing a single turn around the magnet's circumference).

The reduction or elimination of negative current flows allows for lower power supply requirements in certain magnet designs. Certain implementations of such systems are discussed below and exemplary power supply sizes are provided. It should be understood that these particular system designs, and associated power supply sizes are merely exemplary and that other designs and power supply sizes, or ranges of sizes, are contemplated.

Certain implementations herein of a magnetic resonance imaging system can include a resistive, solenoidal electromagnet for whole-body MRI including conductors and ferromagnetic material within an envelope of a gapped electromagnet where the conductors are made of copper. Certain of such implementations, where the conductors are directly cooled, (e.g., coolant is flowed through the center of the conductor) can be configured for a field strength of at least 0.12 Tesla and a power supply of less than 30 kW or less than 45 kW, while others may be configured for a field strength of at least 0.2 Tesla and a power supply of less than 100 kW or less than 145 kW, and yet others may be configured for a field strength of at least 0.3 Tesla and a power supply of less than 210 kW or less than 300 kW. In implementations where the conductors are indirectly cooled (e.g., coolant is flowed around the conductors or the conductors are naturally cooled by the environment around them), such electromagnets may be configured for a field strength of at least 0.12 Tesla and a power supply of less than 35 kW or less than 50 kW, while others may be configured for a field strength of at least 0.2 Tesla and a power supply of less than 105 kW or less than 150 kW, and yet others may be configured for a field strength of at least 0.3 Tesla and a power supply of less than 230 kW or less than 330 kW.

Other implementations herein of a magnetic resonance imaging system can include a resistive, solenoidal electromagnet for whole-body MRI including conductors and ferromagnetic material within an envelope of a gapped electromagnet where the conductors are made of aluminum. Certain of such implementations where the conductors are directly cooled (e.g., coolant is flowed through the center of the conductor), can be configured for a field strength of at least 0.12 Tesla and a power supply of less than 45 kW or less than 65 kW, while others may be configured for a field strength of at least 0.2 Tesla and a power supply of less than 155 kW or less than 220 kW, and yet others may be configured for a field strength of at least 0.3 Tesla and a power supply of less than 335 kW or less than 480 kW. In implementations where the conductors are indirectly cooled (e.g., coolant is flowed around the conductors or the conductors are naturally cooled by the environment around them), such electromagnets may be configured for a field strength of at least 0.12 Tesla and a power supply of less than 50 kW or less than 70 kW, while others may be configured for a field strength of at least 0.2 Tesla and a power supply of less than 170 kW or less than 245 kW, and yet others may be configured for a field strength of at least 0.3 Tesla and a power supply of less than 365 kW or less than 520 kW.

The technologies of the present disclosure, as described above, can reduce power requirements and can result in reduced forces between the two halves of a gapped solenoidal electromagnet. With existing technology, gapped solenoidal electromagnets require substantial fixation structures in order to keep apart the two halves of the magnet, which are attracted to one another with considerable force. This must be done in a way that avoids any relative movement that could affect field homogeneity.

Examples of substantial fixation structures are depicted in FIG. 1 as buttresses 114. Buttresses of this type would normally need to be made from a strong and typically metallic material such as steel or aluminum. However, the technologies of the present disclosure enable implementations of a magnetic resonance imaging system including a resistive, solenoidal electromagnet for whole-body MRI including conductors and ferromagnetic material within an envelope of a gapped electromagnet where the two halves of the electromagnet are held apart by a fixation structure where, in some implementations, the fixation structure may be substantially nonmetallic. "Substantially" nonmetallic is understood to describe a fixation structure that relies primarily on nonmetallic materials to brace against the force exerted by the two magnet halves. To the extent metallic materials are included in such a structure but are not primarily responsible for bearing the load, such a structure is intended to fall within the term "substantially nonmetallic."

In certain implementations, the fixation structures contemplated herein may comprise carbon fiber or zero CTE carbon fiber.

When the technologies above are combined with a radiation therapy device, the combined system may be configured such that the radiation therapy device is directed to treat through the fixation structure. For example, the fixation structure may be a 0.5 cm thick uniform carbon fiber cylinder between the magnet halves, with a coefficient of thermal expansion that is substantially zero and which provides minimal and uniform attenuation of a radiation therapy beam.

In yet another implementation, the fixation structure may be a single cylinder or continuous former that extends not just between the two magnet halves, but also into the electromagnet assembly itself (e.g., as a former between layers of conductors).

The technologies of the present disclosure can lower an electromagnet's current requirements and heating and also reduce forces exerted on a magnet's conductors and structures that support them. These technologies may thus facilitate certain types of beneficial magnet designs and construction methods. For example, in one particular implementation, a magnetic resonance imaging system having a resistive, solenoidal electromagnet for whole-body MRI with a field strength of at least 0.05 Tesla may include conductors for creating a main magnetic field of the electromagnet where the main magnetic field is not generated by bundles of conductors but instead may be generated by layers of conductors.

While cylindrical MRI systems commonly generate their main magnetic field using bundles (i.e., conductors wrapped together and placed at particular, distinct locations), certain implementations of the present disclosure provide for more distributed conductor arrangements, for example, distributed across layers. An example of such a layered conductor arrangement is depicted in FIG. 3, and the details of such designs will be discussed further below. Because such layered arrangements can produce highly homogeneous fields and can facilitate beneficial new fabrication methods, they can provide an alternative to generating main magnetic fields using bundles of conductors. When the present disclosure refers to designs where "the main magnetic field is not generated by bundles of conductors," such means that the main magnetic field is entirely or primarily created by more distributed conductor configurations (e.g., similar to those described with respect to FIG. 3). Nevertheless, the present disclosure contemplates that small amounts of conductor bundles may be used in conjunction with these designs. Thus, the term "main magnetic field is not generated by bundles" herein contemplates some minimal use of bundles, for example, where bundles are used, but contribute no more than 10% to the production of the main magnetic field.

When the present disclosure refers to main magnetic field generation using conductors configured in a "layer," such refers to, for example, conductor loops or coils arranged in a generally cylindrical shape at a radius of the electromagnet, which traverse the majority of the length of the electromagnet (or, in the case of a gapped magnet, the majority of the length of the half of the electromagnet). FIG. 3 illustrates one example of a layered design for a gapped solenoidal magnet where layers of conductors extend or traverse approximately one meter across the magnet's Z axis—from about 0.2 m away from the center of the imaging field to about 1.2 m away from the center of the imaging field.

A main magnetic field can be generated by multiple layers of conductors, as depicted in FIG. 3, and electromagnets with this design may include ferromagnetic material within the magnet envelope, as also depicted in FIG. 3 and as discussed above.

Figure 6:
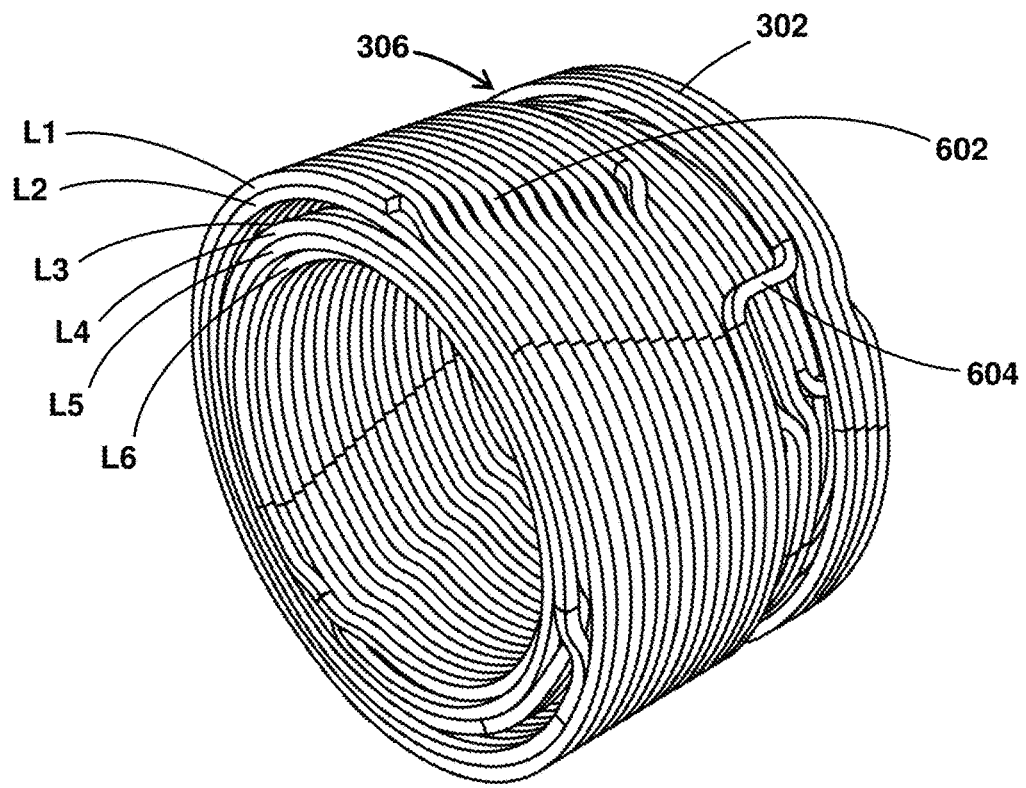
FIG. 6 is a diagram illustrating a simplified perspective view of the conductors of two exemplary halves of a gapped solenoidal electromagnet in accordance with certain aspects of the present disclosure.
Figure 6:
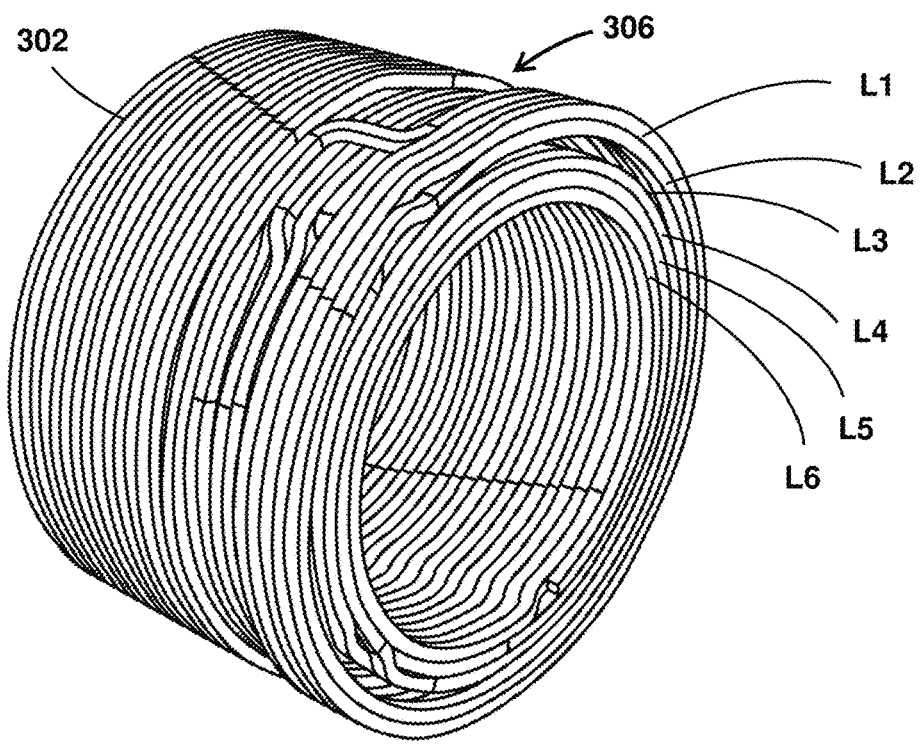

FIG. 6 depicts the exemplary design of FIG. 3 along with an additional view of the design from the opposite perspective. FIG. 6 illustrates five separate layers of conductors for generating a main magnetic field, with level L3 being reserved for the insertion of a ferromagnetic cylinder. The present disclosure contemplates various numbers of layers being used, the number of which, for example, may depend on the particular conductor size chosen. In the implementation of FIG. 6, relatively large conductors are used (e.g., 4 cm by 4 cm, with an open core for direct cooling).

In another implementation, 2 cm by 2 cm conductors may be utilized. In one particular implementation of a resistive, solenoidal electromagnet for whole-body MRI having a field strength of at least 0.05 Tesla and conductors for creating a main magnetic field of the electromagnet, the main magnetic field is generated by layers of conductors where the conductors have a cross-sectional area greater than 0.50 $cm^2$ or greater than 0.75 $cm^2$.

In some implementations, a portion of the conductors can have a smaller cross-sectional area than the cross-sectional area for other conductors. For example, a layer of smaller conductors may have approximately half the cross-sectional size of a layer of larger conductors (e.g., one layer's conductors may have a cross section of 40 mm×40 mm, and another layer may have conductors with a cross-section of 20 mm×20 mm). In some implementations, a layer or layers of smaller conductors may be implemented at or near the outer radial layer, or near or adjacent the ferromagnetic layer (e.g., L3 as shown in FIG. 6).

Layered designs using the technologies of the present disclosure can avoid the need for substantial/strong metallic formers typically used with bundled designs and designs with higher current requirements. Thus, in some implementations, the conductors of the designs contemplated herein may be supported by lower strength materials such as fiberglass or plastic cylindrical formers. For example, the layers of conductors may be supported by 1 mm thick cylindrical fiberglass formers in-between layers, and the conductor layers and formers may be combined into a single rigid object through the use of an epoxy or other insulating material.

Figure 7A:
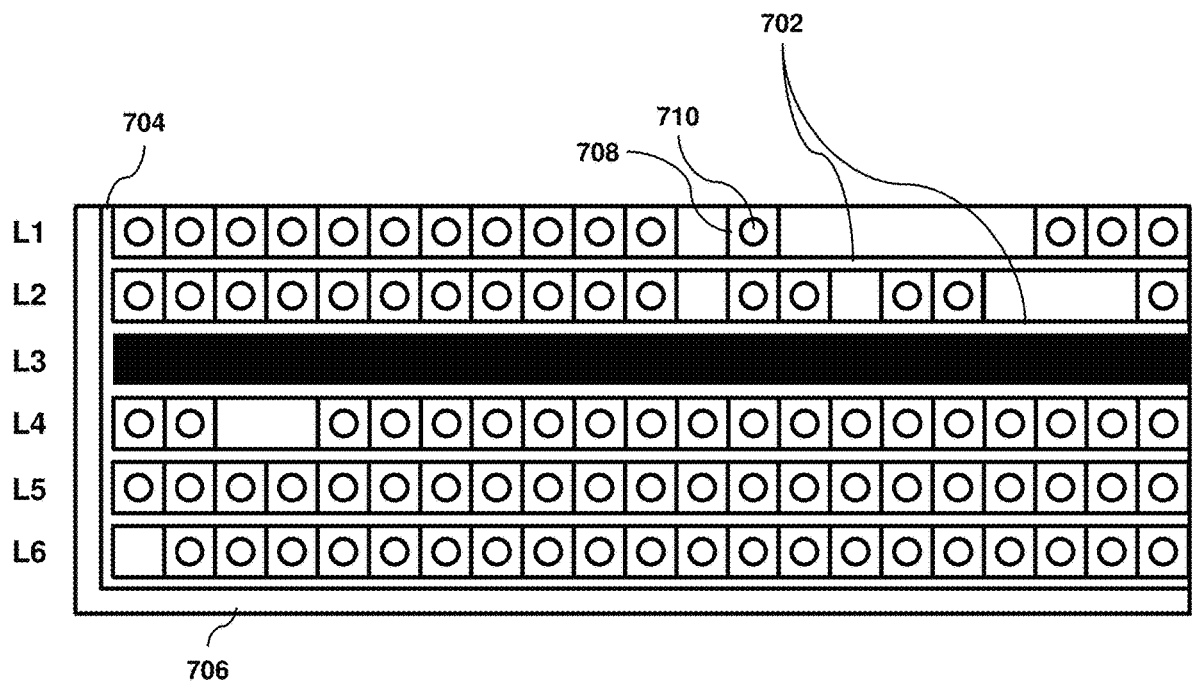
FIG. 7A is a diagram illustrating a simplified exemplary construction of a portion of an electromagnet in accordance with certain aspects of the present disclosure.

FIG. 7A illustrates a cross-section of one particular implementation where conductor layers L1, L2, L4, L5, L6 and ferromagnetic material layer L3 are separated by formers 702 that may be comprised of a nonmetallic material such as a glass reinforced polymer. FIG. 7A illustrates an implementation where the electromagnet may also include a side cheek 704 that can be made from a similar nonmetallic material, and an external former 706, which may optionally be made from a stronger, metallic material such as aluminum.

In one particular implementation, a resistive, solenoidal electromagnet for whole-body MRI, having a field strength of at least 0.05 Tesla, can include conductors for creating a main magnetic field of the electromagnet, where the main magnetic field is generated by layers of conductors and where the electromagnet utilizes non-metallic formers for supporting conductors, for example, fiberglass formers. One implementation includes at least two solenoidal layers of conductors separated by a nonmetallic former. Another implementation may include less than 10 layers of conductors. In yet another implementation, the layers of conductors and non-metallic formers may be constructed to form a rigid object, for example, by fixing them together with an epoxy. In still another implementation, the rigid object can further include at least a portion of a gradient coil. For example, just the slice select coil may be incorporated or, alternatively, the entire gradient coil may be epoxied together with the main magnet into a single rigid object.

FIG. 7A illustrates an example of a conductor 708 having a generally square cross-section with a cylindrical, hollowed-out core 710 that can be used for direct cooling (e.g., the flowing of water or coolant through core 710).

Figure 7B:
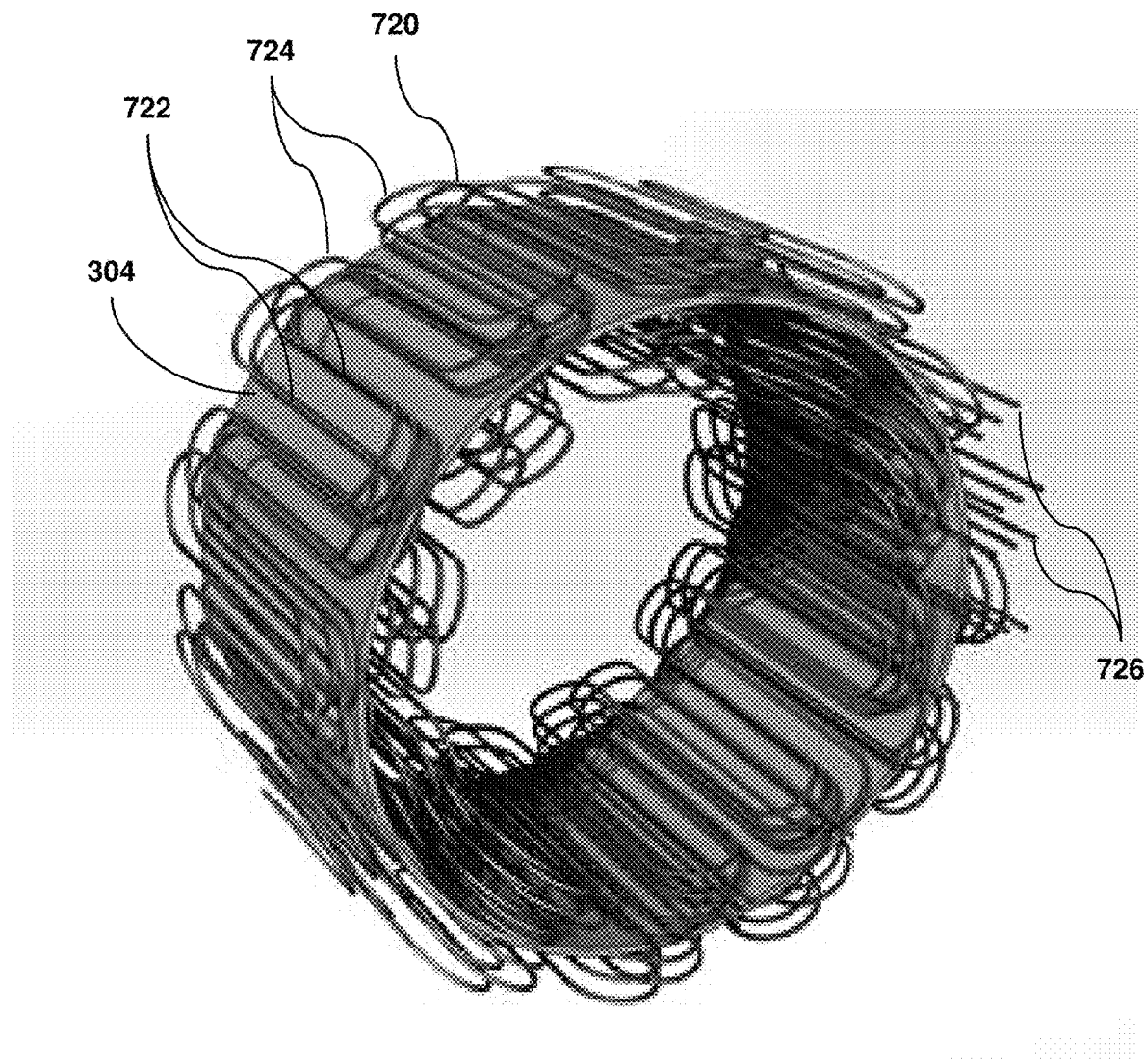
FIG. 7B is a diagram illustrating a simplified perspective view of one half of an electromagnet with an indirect cooling system that includes serpentine channels in accordance with certain aspects of the present disclosure.

FIG. 7B illustrates an example of an electromagnet with an indirect cooling system provided by serpentine coolant channels. In some implementations, the indirect cooling system can provide sufficient cooling for the electromagnet such that some or all of the conductors in the electromagnet may be solid conductors, rather than having a hollow core 710 as shown in the direct cooling example in FIG. 7A.

Figure 7C:
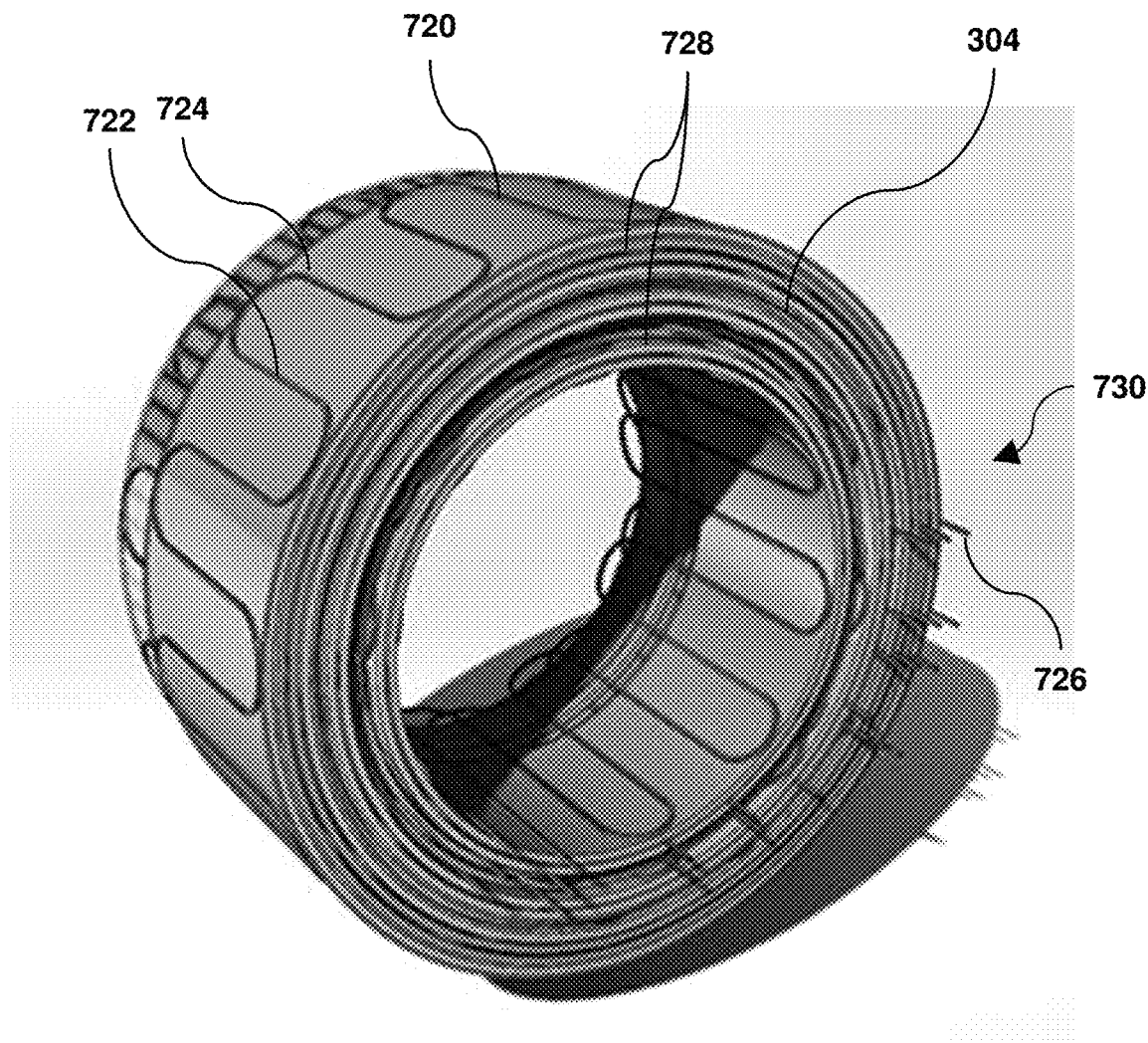
FIG. 7C is a diagram illustrating a simplified perspective view of an indirect cooling system including serpentine channels between electromagnet layers in accordance with certain aspects of the present disclosure.

The present disclosure contemplates indirect cooling systems having various types of cooling channels, for example, saddle-shaped circular loops, helical loops, a serpentine shape, etc. As shown in FIG. 7B, a serpentine channel 720 can include one or more linear sections 722 and one or more curved sections 724, which can combine to form an "S-shaped" or "serpentine" channel 720. In some implementations, a serpentine channel 720 can be adjacent (or wrapped around) one or more of the conductors or ferromagnetic layers to provide indirect cooling. FIG. 7C illustrates an exemplary indirect cooling system, such as depicted in FIG. 7B, with its serpentine channels interspersed between layers of conductors and/or ferromagnetic material.

A serpentine channel 720 will include an inlet and outlet (e.g., 726) for flowing coolant through the channel. In some implementations, the inlets and/or outlets can be located at a particular end 730 of the electromagnet that may be more accessible for establishing cooling connections. For example, inlets and outlets may be located at a patient end or a service end of the electromagnet.

When the present disclosure refers to a solenoidal electromagnet or refers to a solenoidal layer of conductors within an electromagnet, it is contemplated that the conductors may deviate somewhat from a perfect solenoid (i.e., a uniform, helically wound coil). For example, a layer of conductors may include S-bends (illustrated as element 602 in FIG. 6).

S-bend configurations are an alternative to helical configurations. In addition to having a different manufacturing process, they can be modeled more effectively during magnet design if the software used for modeling simplifies current loops as pure "rings" of current (in which case, S-bend designs will more closely match the model than helical designs).

As referred to herein, an "S-bend" may take the form of a stretched-out letter S, as shown in the figures, but the term is intended to cover any gradual or sharp transition (even a 90 degree turn) to a subsequent loop that results in current flow in the subsequent loop continuing in the same circumferential direction. S-bends are distinguished from helical arrangements and also from U-bends, which result in current flow of the subsequent loop going in the opposite direction.

As previously discussed, certain electromagnet designs may include negative currents therein (i.e., those which create a magnetic field counteracting the direction of the main magnetic field). If such negative currents are required, they can be implemented in the coils of the present disclosure utilizing U-bends. As noted, however, negative currents may be avoided using the technologies of the present disclosure, including the inclusion of ferromagnetic material within the envelope of the electromagnet.

In certain implementations, conductors may also be arranged so that a conductor traverses a layer in a direction parallel to the axis of the solenoidal electromagnet. Such an arrangement is depicted as 604 in FIG. 6 and can be utilized when magnet modeling and design indicates that a current loop is not required at a specific axial location within that layer. For further illustration, such a location is depicted in the exemplary design of FIG. 3 as element 306.

In one particular implementation, a resistive, solenoidal electromagnet for whole-body MRI having a field strength of at least 0.05 Tesla can include conductors for creating a main magnetic field of the electromagnet, where the main magnetic field is generated by layers of conductors and where the layers of conductors include at least one layer including a section where a conductor traverses in a direction parallel to an axis of the solenoidal electromagnet and where the conductor may have a cross-sectional area greater than 0.50 cm$^2$ or greater than 0.75 cm$^2$.

In some implementations, the layers of conductors may include a first layer that is a helically wrapped conductor having a first helical tilt and a second layer, adjacent to the first layer, comprising a helically wrapped conductor having a second helical tilt, where the second helical tilt is opposite to the first helical tilt. In other words, certain implementations may have a layer that is a helically wound conductor tilting to the right and the layer just inside or outside of that layer (i.e., the layer adjacent at the immediately smaller or larger radius) is a helically wound conductor tilting to the left.

Figure 8A:
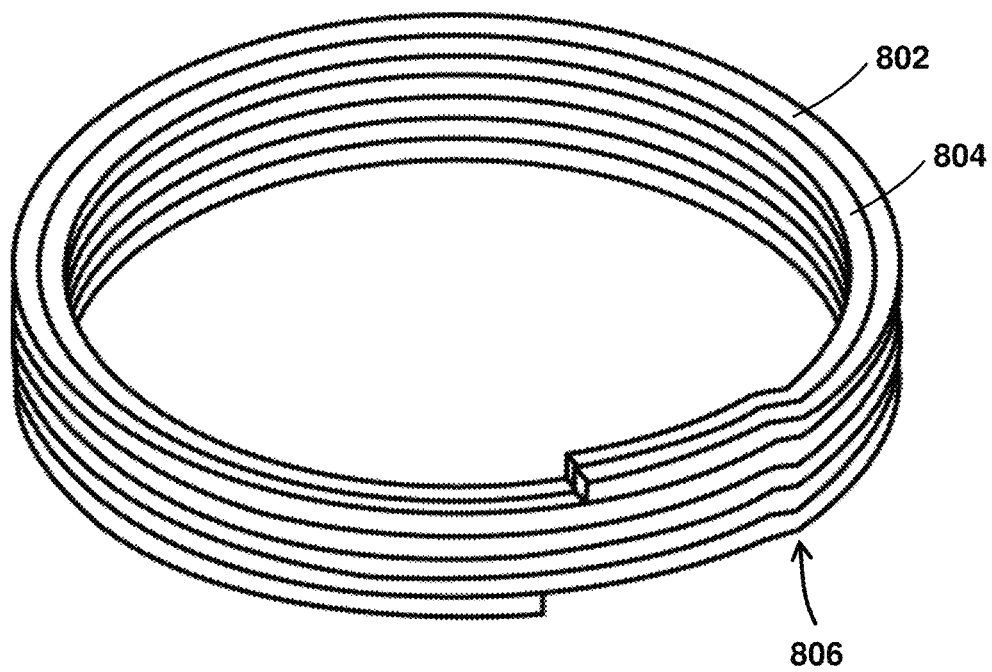
FIG. 8A is a diagram illustrating two exemplary arrangements for conductors in adjacent levels within an electromagnet in accordance with certain aspects of the present disclosure.
Figure 8A:
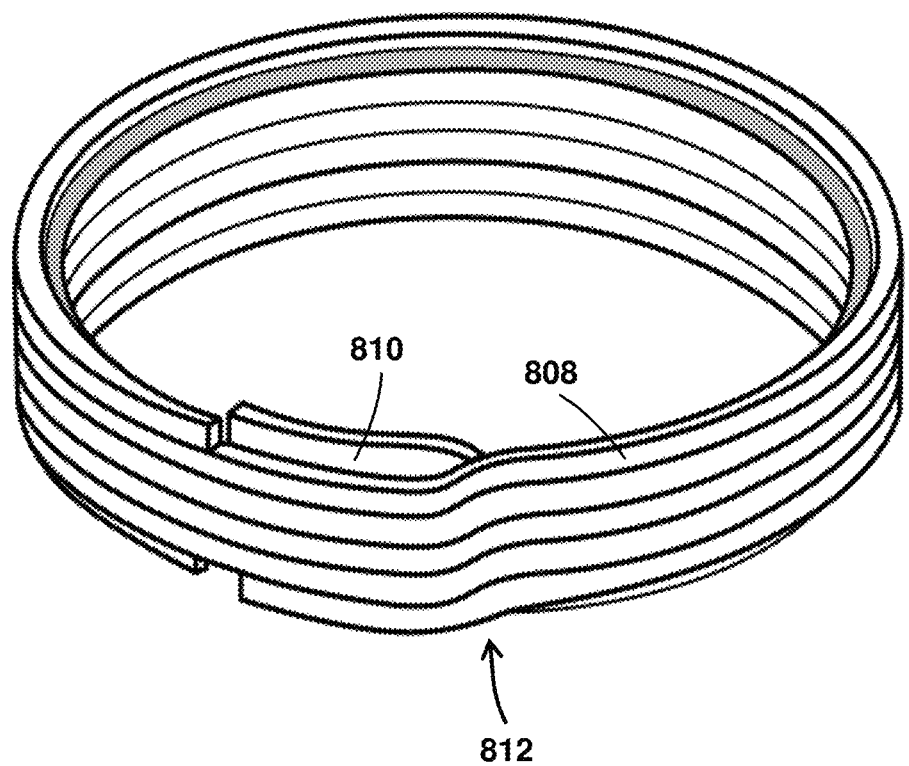

In other implementations that are similarly designed to facilitate the production of a homogeneous magnetic field, the layers of conductors may include a first layer of wrapped conductor having first S-bends bending in a first direction and a second layer, adjacent to the first layer, comprising a wrapped conductor having second S-bends bending in a second direction where the first S-bends and the second S-bends overlap and where the second direction is opposite to the first direction. An example of such a configuration is depicted at the bottom of FIG. 8A where the outer layer 808 has S-bends in one direction and the adjacent layer 810 has S-bends bending in the opposite direction and where the S-bends of each layer overlap at location 812. An alternative arrangement is depicted at the top of FIG. 8A where the S-bends overlap, but do not bend in opposite directions.

Figure 8B:
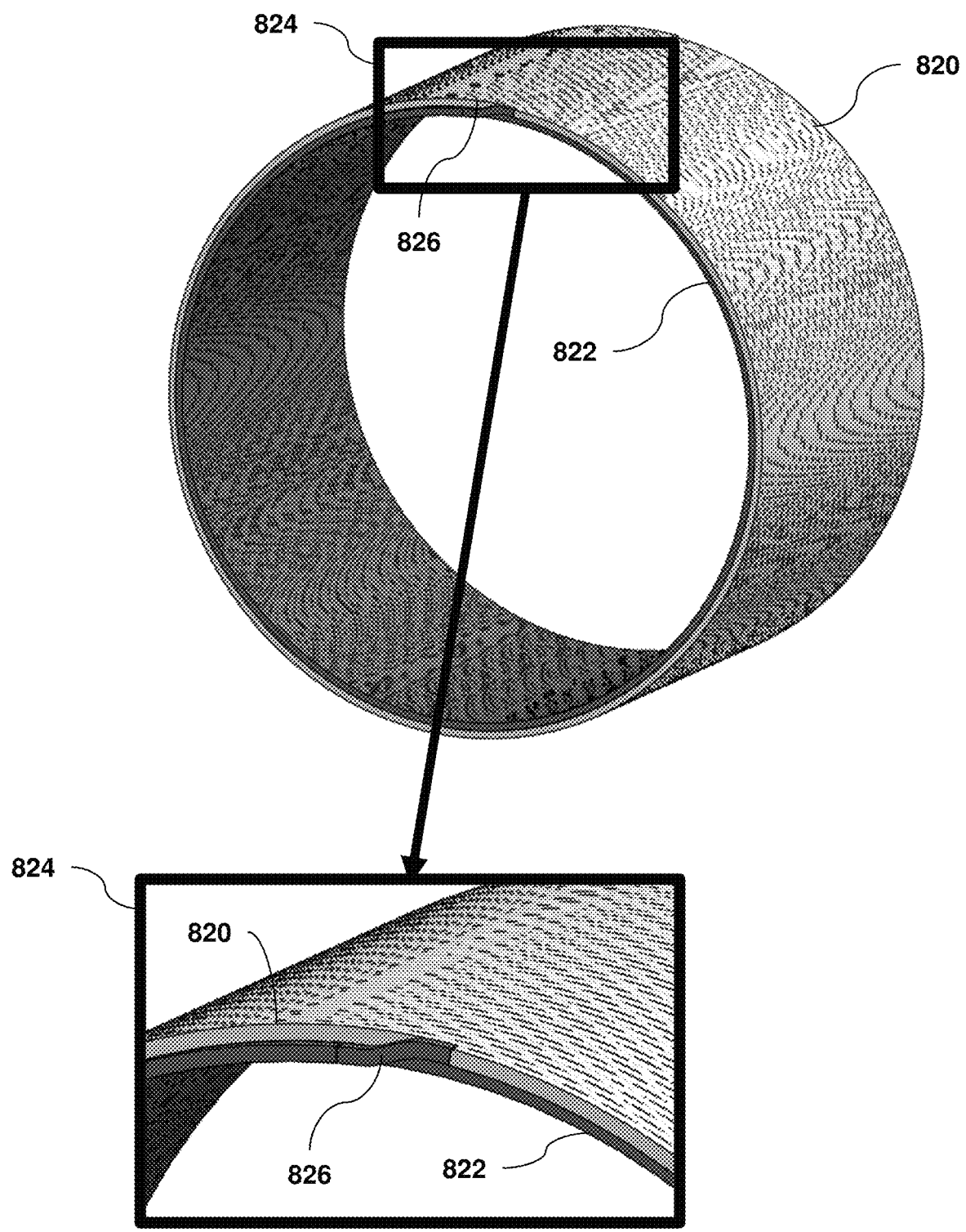
FIG. 8B is a diagram illustrating a simplified exemplary construction of a portion of an electromagnet with radial S-bends in accordance with certain aspects of the present disclosure.

FIG. 8B is a diagram illustrating a simplified exemplary construction of a portion of an electromagnet with radial S-bends in accordance with certain aspects of the present disclosure. In some implementations, adjacent layers of conductors can be connected (e.g., in a generally radial direction) by one or more S-bends 826. An example of such a configuration is illustrated in FIG. 8B showing two adjacent layers of conductors where a first layer 820 of wrapped conductor is connected to a second layer 822 of wrapped conductor by an S-bend 826. An expanded view 824 of the S-bend connection is also shown. In some embodiments, either or both of the adjacent layers can be helical (e.g., not including S-bends in the axial direction) or they may include S-bends in the axial direction instead of having a helical pitch).

Figure 8C:
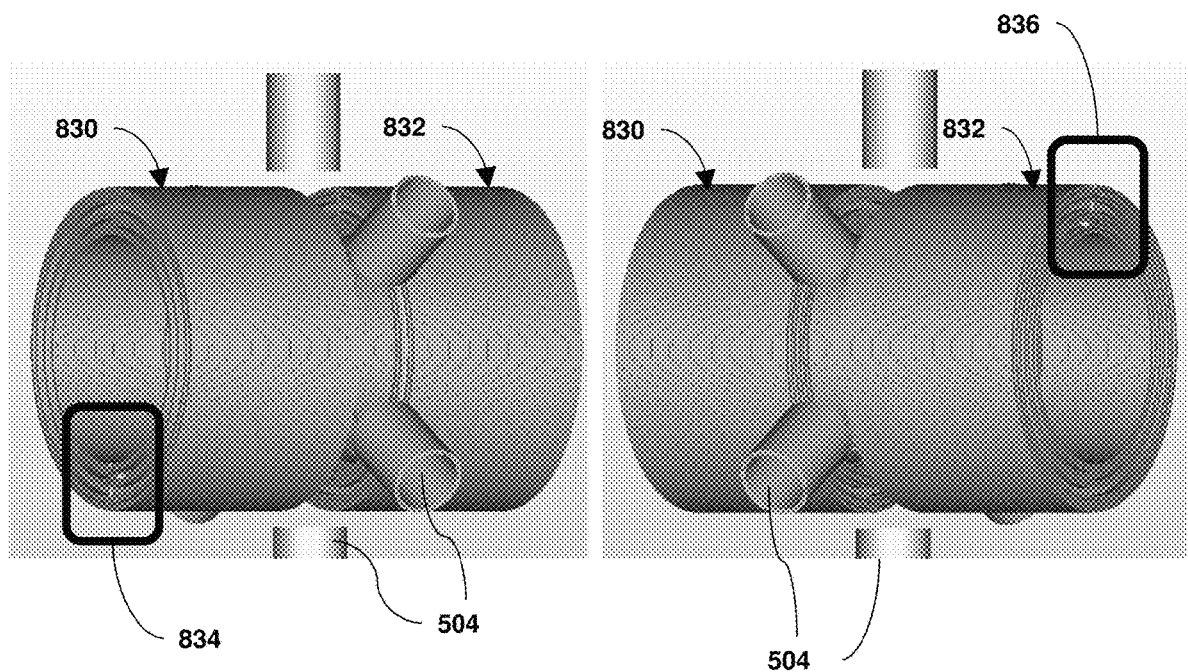
FIG. 8C is a diagram illustrating a simplified exemplary configuration of an electromagnet in accordance with certain aspects of the present disclosure.

FIG. 8C is a diagram illustrating a simplified exemplary configuration of an electromagnet in accordance with certain aspects of the present disclosure. This exemplary configuration includes a gapped electromagnet design and happens to depict cylinders arranged in the gap that may be used in a radiotherapy application to shield components of a linear accelerator. In certain implementations, the magnet halves (830, 832) can be "rotated" such that their radial connections 834 (e.g., S-bends) between adjacent layers of conductors are not at the same azimuthal angle. This can have the beneficial effect of reducing remnant tesseral harmonics that may be generated by the radial S-bend connections. As shown in the example illustrated in FIG. 8C, the magnet halves can be rotated approximately 180 degrees relative to each other, though other rotation angles could be implemented, for example, 30°, 45°, 60°, 90°, 135°, 150°, 165°, etc. One of the magnet halves may be designated the "patient end" (where the patient enters bore 200 of the MRI system) and the other magnet half can be designated the "service end." In one implementation, the patient-end radial connections 834 can be on the bottom (i.e., at the lowest point of patient-end magnet half 830), and service-end radial connections 836 can be on the top (i.e., at the highest point of service-end magnet half 832). In other implementations, the angle of the magnet halves can be different (e.g., having an overall rotation of 30°, 45°, 60°, 90°, 135°, 150°, 165° relative to the vertical, such that the radial connections are not at the top and bottom), while still maintaining an approximately 180 degree separation between the radial connections of the two magnet halves.

In exemplary magnet designs of the present disclosure, multiple layers of conductors can be connected (for example, L1, L2, L4, L5 and L6 of FIG. 3) so that they essentially form a single current path. Thus, the electromagnet may be configured to operate with a single supplied current. The layer to layer connections can be made so that the current flow will be positive in each layer and therefore each layer will positively contribute to creation of the main magnetic field. In the case of a gapped magnet, the magnet halves may be connected in series and therefore still run on a single supplied current (or they may run in parallel circuits, but on the same amperage). Such beneficial configurations can utilize simplified power supplies, in contrast to typical bundled magnet designs that often require different amperages for different bundles (and often require a negative current in one or more bundles).

Figure 9:
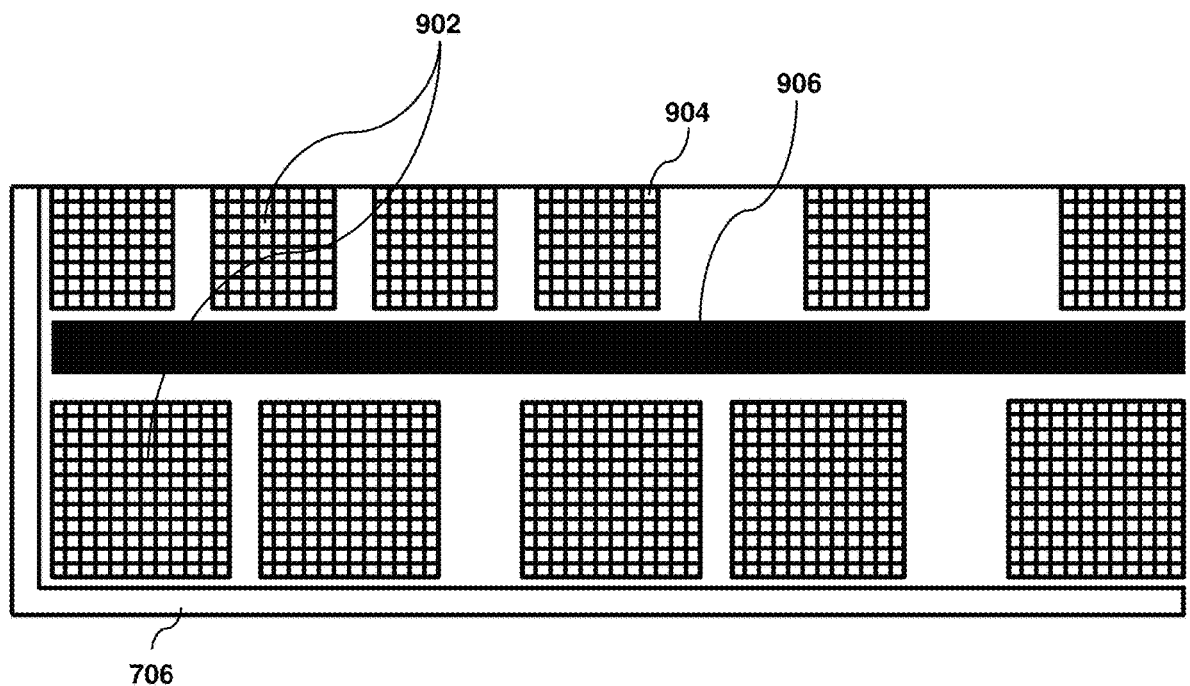
FIG. 9 is a diagram illustrating a simplified exemplary alternative construction of a portion of an electromagnet in accordance with certain aspects of the present disclosure.

FIG. 9 depicts an alternative electromagnet design that is not based on layers of conductors, but that similarly has a more distributed conductor arrangement for the creation of the main magnetic field. Exemplary embodiments of such designs include conductors covering, for example, at least 40%, 50%, 60% or 70% of the magnet envelope. The particular exemplary implementation depicted in FIG. 9 has conductors covering more than 50% of the magnet envelope and utilizes conductor bundles 902 in creating the main magnetic field. While many electromagnet designs that utilize bundles to generate their main magnetic field can utilize very small conductors, the present disclosure also contemplates the utilization of larger conductors in bundles. In one particular example, depicted in FIG. 9, individual conductors 904 have a cross-section of 1 cm×1 cm.

Implementations of this type of design may also include ferromagnetic material within the magnet envelope, as previously discussed. One example of such is depicted as ferromagnetic material 906 in FIG. 9 and can enable the electromagnet to be configured for current flow in only one circumferential direction within the magnet. For example, each of the bundles driving the main magnetic field may have a positive current direction. In other embodiments, the electromagnet may be configured for less than 5% negative current flow or less than 10% negative current flow. In one implementation, bundles may be connected by conductors traversing in a direction parallel to the axis of the electromagnet to essentially form a single current path and to allow the electromagnet to be powered with a single supplied current.

Electromagnets, especially those used in magnetic resonance imaging, can be required to produce highly homogeneous and stable magnetic fields. Such stability is commonly facilitated by the use of sophisticated DC power supplies that maintain highly stable voltage and current outputs (for example, on the order of only parts per million fluctuation). However, the technologies of the present disclosure can provide for homogeneous and stable magnetic fields without the need for such complex power supply designs. These technologies are applicable to different magnet configurations such as traditional solenoidal (ungapped) magnets, gapped solenoidal systems, dipolar magnets, etc.

When the present disclosure refers to electromagnets for magnetic resonance imaging, it is presumed that such magnets and their power supplies are configured to result in the requisite imaging field homogeneity and stability required for such MR imaging (e.g., on the order of parts per million). When "power supply(-ies)" are referred to herein, this terminology is intended to cover the electronics responsible for supplying the electromagnet with its requisite power including any associated electronics for rectification, filtering, control, etc. it is contemplated that such electronics may be present in a single unit or may be dispersed in different locations or modules. It is also understood herein that power supplies can be configured to provide a single current or may be multi-channel power supplies to provide multiple, potentially differing, currents.

While power supplies for MRI systems are typically designed to provide DC current with fluctuations on the order of only parts per million, the technologies of the present disclosure can provide the requisite field homogeneity and stability with a power supply having, e.g., only part per ten thousand stability. In one example, this stability metric can relate to the DC current ripple that exists, after rectification, at the original AC frequency and harmonics thereof. For example, implementations of the present disclosure may utilize a power supply having at least one part per ten thousand current fluctuation at frequencies of 180 Hz or above, or at frequencies of 600 Hz or above. Other implementations may even utilize power supplies having at least one part per thousand current fluctuation at frequencies of 180 Hz or above, or at frequencies of 600 Hz or above.

The relatively high current fluctuations in such power supplies can be filtered out essentially via the complex impedance of the wound metal conductors in various of the electromagnet designs disclosed herein. In one particular example discussed below, an exemplary electromagnet can filter current fluctuations of 15 parts per ten thousand over 600 Hz down to a level of −90 dB. Implementations of the present disclosure can thus include magnetic resonance imaging systems that do not include a current filter separate from the filtering provided by the resistive electromagnet itself. Stated another way, such a system does not include an additional element added for the purpose of reducing current fluctuation (e.g., the addition of an inductor).

Alternative implementations may include a current filter but can limit such filters to having less than, for example, 5 mH, 2 mH or 1 mH inductance. One particular implementation of a magnetic resonance imaging system can thus include a resistive electromagnet for whole-body MRI having a field strength of at least 0.05 Tesla and a power supply for powering the resistive electromagnet having at least one part per ten thousand current fluctuation at frequencies of 180 Hz or above and either no current filter separate from the filtering provided by the resistive electromagnet itself, or a current filter of less than 2 mH inductance.

Certain implementations of the technologies described herein also enable the use of single-channel power supplies. For example, certain electromagnet designs described herein as having ferromagnetic material within their magnet envelope can be supplied with a single current. As noted above, these magnet designs can be optimized, for example, to avoid a need for negative currents and/or bundles of conductors that must be supplied with differing amounts of current. As a result, simplified, single-channel power supplies can be used that do not require complex control systems to keep multiple power channels in sync with one another. Furthermore, low-frequency current fluctuations from a single-channel power supply can be more easily handled by MRI control systems accounting for such variations than fluctuations from multichannel power supplies. For example, an MRI's spectrometer may be utilized to compensate for low-frequency drifts in current or voltage through main magnetic field strength corrections.

In certain implementations, these power supplies can be used with the exemplary gapped solenoidal magnet designs discussed above. For example, in an implementation utilizing directly cooled aluminum conductors where the electromagnet has a field strength of at least 0.12 Tesla, the power supply can be designed to provide a power of only 45 kW, or even less. Or, a power supply of 155 kW or less may be used for such a design and a field strength of at least 0.2 Tesla. Other configurations as taught or specifically discussed herein are contemplated.

While even single-channel power supplies for MRIs typically require complex control systems to minimize current and voltage fluctuations, the present disclosure contemplates the use of a power supply that does not include active current controls, (e.g., the utilization of current feedback loops).

Figure 10:
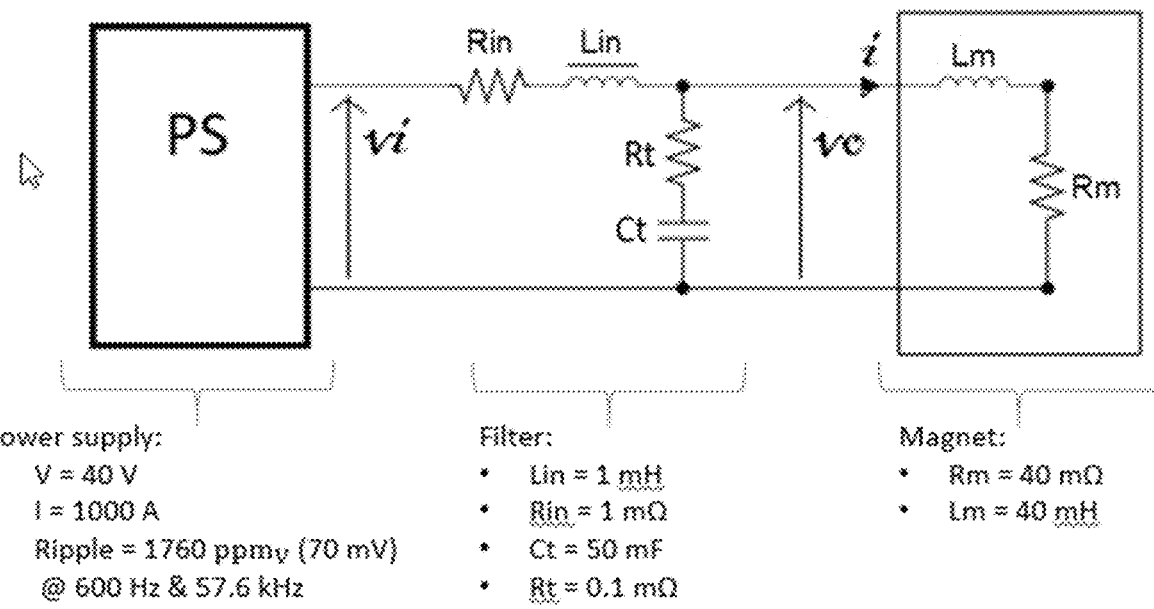
FIG. 10 is a simplified circuit diagram illustrating an exemplary electromagnet and associated power supply with filtering in accordance with certain aspects of the present disclosure.

Implementations of the present disclosure contemplate the addition of a simple filter to control voltage fluctuations, for example, an LC filter. In one exemplary implementation, similar to the designs disclosed above, a solenoidal electromagnet having a gap of 28 cm configured for whole body MRI with a field strength of at least 0.12 Tesla is considered, and is made with ferromagnetic material within the magnet envelope and directly cooled aluminum conductors. An exemplary filter for such a design is depicted in FIG. 10. FIG. 10 depicts this exemplary electromagnet having a resistance of 40 mΩ and an inductance of 40 mH. The power supply utilized can be configured to provide 1000 A at 40 V and can have a ripple of 1760 ppm at 600 Hz and 57.6 kHz. In this example, a filter may be used with Lin=1 mH, Rin=1 mΩ, Ct=50 mF, and Rt=0.1 mΩ. Such filter characteristics may be determined with the assistance of the following equations:

$$\frac{V_o}{V_i} = \frac{(R_m + L_m S)(1 + C_t R_t S)}{R_{in} + R_m + (L_{in} + L_m + C_t R_{in} R_m + C_t(R_{in} + R_m)R_t)S + C_t(L_m(R_{in} + R_t) + L_{in}(R_m + R_t))S^2 + C_t L_{in} L_m S^3}$$

$$\text{TF\_Y}(S) = \frac{I}{V_L} = \frac{1 + C_t R_t S}{R_{in} + R_m + (L_{in} + L_m + C_t R_{in} R_m + C_t(R_{in} + R_m)R_t)S + C_t(L_m(R_{in} + R_t) + L_{in}(R_m + R_t))S^2 + C_t L_{in} L_m S^3}$$

These equations represent the transfer function (dynamic response) of the system. A Bode plot of the magnitude can show the magnitude response as a function of the frequency (the high frequency components are effectively filtered). Such plots (or equivalent calculations of the transfer function) can be implemented to design the filter to reduce the magnitude of the ripple at unwanted frequencies above a low frequency cut off.

In alternative implementations, a battery or multiple batteries may be utilized in the system to at least partially limit the power supply fluctuations. Such may be utilized in addition to or instead of the filters discussed above. In one implementation, the electromagnet may be connected to and essentially powered by the battery and the system can be configured so that the battery can be charged by the power supply.

Power fluctuations at the electromagnet that may be caused by the power supply charging the battery can be avoided by other implementations utilizing multiple batteries (e.g., two or more). In such implementations, the battery responsible for powering the electromagnet can avoid being charged while it is powering the magnet and then, when the battery powering the electromagnet needs to be charged, the power source for the electromagnet can be switched to a different battery that has already been charged. Stated another way, the system may be configured such that the resistive electromagnet can be connected to one of a plurality of batteries while another of the plurality of batteries can be charged by the power supply.

Figure 11:
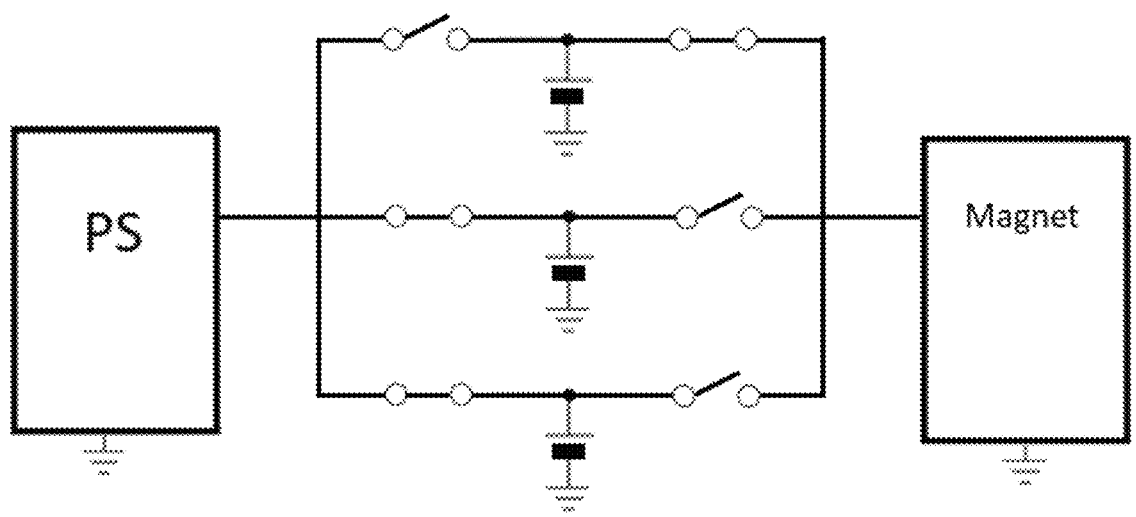
FIG. 11 is a diagram illustrating a simplified implementation for using multiple batteries in conjunction with powering an electromagnet in accordance with certain aspects of the present disclosure.
Figure 11:
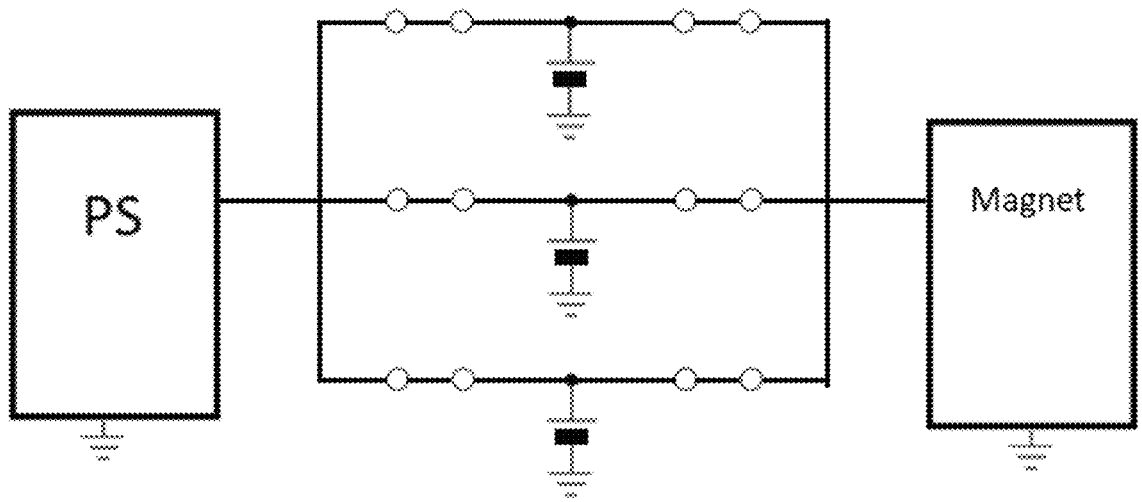

Another example of a multi-battery embodiment is depicted in FIG. 11 and utilizes at least three batteries. As depicted at the top of FIG. 11, switches may be opened and closed so that a single battery is powering the electromagnet (but not being charged at the same time), while the other batteries can be charged. When the initial battery needs to be charged, the switch positions may be changed in a manner that allows the electromagnet to be switched to being powered by another battery that has already been cut off from the power supply. For example, the switch connecting the second battery for charging can be opened prior to the switch between the second battery and the electromagnet being closed for powering the magnet. Such a system having three or more batteries can thus be configured to facilitate a smooth transition between two batteries that are not being charged and not being affected by the fluctuations of the power supply. Stated another way, the system may include at least three batteries and may be configured such that the resistive electromagnet can be connected to a first battery while a second battery is being charged and the system can be further configured for the resistive electromagnet connection to be switched to a third battery that is not being charged when the connection is switched.

If desired, as shown at the bottom of FIG. 11, all of the batteries may be charging and connected to the electromagnet to keep it warm when the electromagnet is not in use (e.g., when MRI imaging is not occurring, such as between patients).

Figure 12:
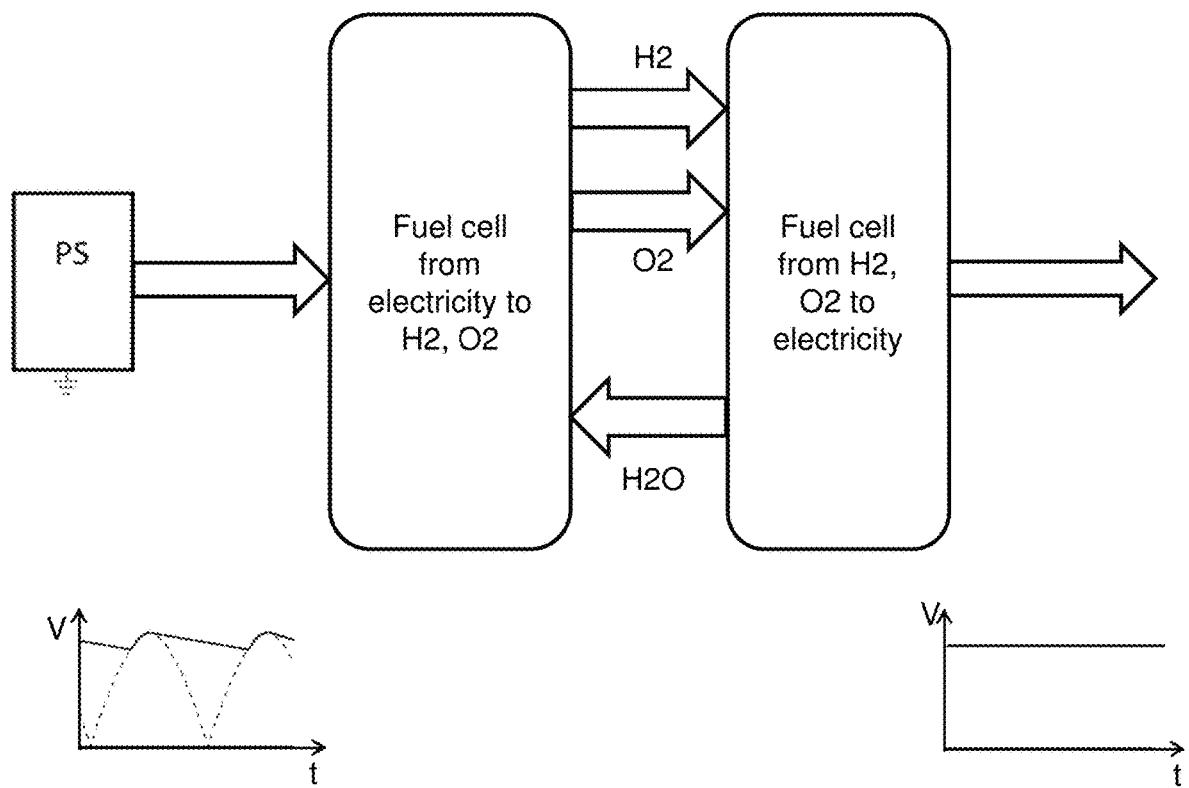
FIG. 12 is a diagram illustrating a simplified implementation of a fuel-cell between a power supply and an electromagnet in accordance with certain aspects of the present disclosure.

While a battery or multiple batteries may be used to shield an electromagnet from power source fluctuations, the present disclosure also contemplates the use of a fuel-cell in a similar manner. For example, as depicted in FIG. 12, the system may be configured so that a fuel cell is located between the power supply and the resistive electromagnet to essentially filter out voltage fluctuations seen at the power supply.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can be a non-transitory, machine-readable medium that can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A magnetic resonance imaging (MRI) system comprising:
   a resistive, solenoidal electromagnet for whole-body MRI having a field strength of at least 0.05 Tesla comprising:
   conductors for creating a main electromagnetic field of the electromagnet;
   wherein the main electromagnetic field is not generated by bundles of conductors.

2. A magnetic resonance imaging (MRI) system comprising:
   a resistive, solenoidal electromagnet for whole-body MRI having a field strength of at least 0.05 Tesla comprising:
   conductors for creating a main electromagnetic field of the electromagnet;
   wherein the main electromagnetic field is generated by layers of conductors.

3. The system of claim 2, wherein the electromagnet has less than 10 layers of conductors.

4. The system of claim 2, further comprising ferromagnetic material within an envelope of the electromagnet.

5. The system of claim 2, wherein the electromagnet is configured for current flow in only one circumferential direction within the electromagnet.

6. The system of claim 2, wherein the electromagnet is configured to operate with a single supplied current.

7. The system of claim 2, wherein the electromagnet is gapped.

8. The system of claim 2, wherein the electromagnet utilizes non-metallic formers for supporting conductors.

9. The system of claim 2, wherein the electromagnet utilizes fiberglass formers for supporting conductors.

10. The system of claim 8, wherein the layers of conductors and non-metallic formers are constructed to form a rigid object.

11. The system of claim 10, wherein the layers of conductors and non-metallic formers are constructed to form a rigid object by fixing together with an epoxy.

12. The system of claim 10, wherein the rigid object includes at least a portion of the gradient coil.

13. The system of claim 2, wherein the conductors have a cross-sectional area greater than 0.5 centimeters squared.

14. The system of claim 13, wherein the conductors include at least two solenoidal layers of conductors separated by a non-metallic former.

15. The system of claim 2, wherein the layers of conductors comprise:
    a first layer comprising helically wrapped conductor having a first helical tilt; and
    a second layer, adjacent to the first layer, comprising helically wrapped conductor having a second helical tilt;

wherein the second helical tilt is opposite to the first helical tilt.

16. The system of claim 2, wherein the layers of conductors comprise:
   a first layer comprising a wrapped conductor having first S-bends bending in a first direction; and
   a second layer, adjacent to the first layer, comprising a wrapped conductor having second S-bends bending in a second direction.

17. The system of claim 16, wherein the first S-bends and the second S-bends overlap and the second direction is opposite to the first direction.

18. The system of claim 2, wherein the layers of conductors comprise:
   at least one layer including a section where a conductor traverses in a direction parallel to an axis of the solenoidal electromagnet.

19. The system of claim 18, wherein the conductor traversing in the direction parallel to the axis of the solenoidal electromagnet has a cross-sectional area greater than 0.5 centimeters squared.

20. The system of claim 2, wherein the electromagnet has two halves and the two halves are held apart by a fixation structure.

21. The system of claim 20, wherein the fixation structure is substantially nonmetallic.

22. The system of claim 21, wherein the fixation structure comprises carbon fiber.

23. The system of claim 21, further comprising a radiation therapy device, wherein the system is configured such that the radiation therapy device is directed to treat through the fixation structure.

24. A magnetic resonance imaging (MRI) system comprising:
   a resistive, solenoidal electromagnet for whole-body MRI having a field strength of at least 0.05 Tesla comprising:
   conductors for creating a main electromagnetic field of the electromagnet;
   wherein the main electromagnetic field is generated by conductors covering at least 50% of an envelope of the electromagnet.

25. The system of claim 24, wherein the conductors have a cross-sectional area greater than 0.5 centimeters squared.

* * * * *